(12) United States Patent
Velazquez et al.

(10) Patent No.: US 10,493,163 B2
(45) Date of Patent: *Dec. 3, 2019

(54) DENDRIMER CONJUGATES FOR COATING CELLS

(71) Applicant: UNIVERSITY OF MIAMI, Miami, FL (US)

(72) Inventors: Omaida Velazquez, Miami, FL (US); Sylvia Daunert, Miami, FL (US); Pirouz Daftarian, Miami, FL (US); Zhao-Jun Liu, Miami, FL (US); Sapna Deo, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 120 days.

This patent is subject to a terminal disclaimer.

(21) Appl. No.: 15/639,473

(22) Filed: Jun. 30, 2017

(65) Prior Publication Data

US 2018/0050111 A1 Feb. 22, 2018

Related U.S. Application Data

(63) Continuation of application No. 14/403,107, filed as application No. PCT/US2013/042071 on May 21, 2013, now Pat. No. 9,737,611.

(60) Provisional application No. 61/649,607, filed on May 21, 2012.

(51) Int. Cl.
| | |
|---|---|
| *A61K 47/58* | (2017.01) |
| *A61K 49/00* | (2006.01) |
| *C07K 14/705* | (2006.01) |
| *A61K 35/28* | (2015.01) |
| *A61K 47/54* | (2017.01) |
| *A61K 47/64* | (2017.01) |
| *A61K 38/00* | (2006.01) |

(52) U.S. Cl.
CPC .............. *A61K 47/58* (2017.08); *A61K 35/28* (2013.01); *A61K 47/54* (2017.08); *A61K 47/6425* (2017.08); *A61K 49/0004* (2013.01); *C07K 14/705* (2013.01); *C07K 14/70503* (2013.01); *C07K 14/70596* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,507,466 A | 3/1985 | Tomalia et al. | |
| 4,558,120 A | 12/1985 | Tomalia et al. | |
| 4,568,737 A | 2/1986 | Tomalia et al. | |
| 4,587,329 A | 5/1986 | Tomalia et al. | |
| 4,631,337 A | 12/1986 | Tomalia et al. | |
| 4,694,064 A | 9/1987 | Tomalia et al. | |
| 4,713,975 A | 12/1987 | Tomalia et al. | |
| 4,737,550 A | 4/1988 | Tomalia et al. | |
| 4,857,599 A | 8/1989 | Tomalia et al. | |
| 4,871,779 A | 10/1989 | Tomalia et al. | |
| 6,113,946 A | 9/2000 | Szoka et al. | |
| 7,402,560 B2 | 7/2008 | Ronn et al. | |
| 9,737,611 B2 | 8/2017 | Velazquez et al. | |
| 2005/0003431 A1 | 1/2005 | Wucherpfennig et al. | |
| 2010/0112026 A1 | 5/2010 | Karp et al. | |
| 2011/0034422 A1* | 2/2011 | Kannan ................ | A61K 9/0048 514/152 |
| 2011/0098225 A1 | 4/2011 | Berezin et al. | |
| 2015/0139904 A1 | 5/2015 | Velazquez et al. | |

FOREIGN PATENT DOCUMENTS

| | | |
|---|---|---|
| WO | WO 1984/002705 A1 | 7/1984 |
| WO | WO 2013/177197 A1 | 11/2013 |

OTHER PUBLICATIONS

Koch et al. Angiogenesis mediated by soluble forms of E-selectin and vascular cell adhesion molecule-1. 1995 Nature 376: 517-519. (Year: 1995).*
Boyd, Ben J., et al. "Cationic poly-L-lysine dendrimers: pharmacokinetics, biodistribution, and evidence for metabolism and bioresorption after intravenous administration to rats." Molecular Pharmaceutics (2006); 3.5: 614-627.
Bulte et al. "Magnetodendrimers allow endosomal magnetic labeling and in vivo tracking of stem cells." Nat. Biotechnol. (2001); 19: 1141-1147.
Castilla, Diego M., et al. "A novel autologous cell based therapy to promote diabetic wound healing." Annals of Surgery (2012); 256.4: 560-572.
Gardikis, Konstantinos, et al. "Dendrimers and the development of new complex nanomaterials for biomedical applications." Current Medicinal Chemistry (2012); 19.29: 4913-4928, 34 pages.
Goldschmidt-Clermont, Pascal J., et al. "Atherosclerosis, inflammation, genetics, and stem cells: 2012 update." Current Atherosclerosis Reports (2012); 14.3: 201-210.
Goldschmidt-Clermont, Pascal J., et al. "Inflammation, stem cells and atherosclerosis genetics." Current Opinion in Molecular Therapeutics (2010); 12.6: 712-723.
International Search Report, PCT appl. No. PCT/US2013/042071, 3 pages (dated Oct. 21, 2013).
International Preliminary Report on Patentability for International Application No. PCT/US2013/042071, dated Nov. 25, 2014, 5 pages.
Kawamura, Nobuko, et al. "Lipoteichoic Acid-Induced Neutrophil Adhesion via E-Selectin to Human Umbilical Vein Endothelial-Cells (HUVECs)." Biochemical and Biophysical Research Communications (1995); 217.3: 1208-1215.
Liu, Zhao-Jun, et al. "Identification of E-Selectin as a Novel Target for the Regulation of Post-Natal Neovascularization: Implications for Diabetic Wound Healing." Annals of Surgery (2010); 252.4: 625-634.

(Continued)

*Primary Examiner* — Jennifer A. Lamberski
(74) *Attorney, Agent, or Firm* — Cooley LLP

(57) ABSTRACT

The present invention provides dendrimer conjugates. The present invention provides a composition comprising a dendrimer conjugate and a cell, such as a cell covered with dendrimer conjugates, in which dendrimer conjugates home the cell to a target tissue.

10 Claims, 12 Drawing Sheets

(56) References Cited

OTHER PUBLICATIONS

Liu, Zhao-Jun, et al. "Inhibition of endothelial cell proliferation by Notch1 signaling is mediated by repressing MAPK and PI3K/Akt pathways and requires MAML1." The FASEB Journal (2006); 20.7: 1009-1011.

Liu, Zhao-Jun, et al. "Inhibition of tumor angiogenesis and melanoma growth by targeting vascular E-selectin." Annals of Surgery (2011); 254.3: 450-457.

Liu, Zhao-Jun, et al. "Notch activation induces endothelial cell senescence and pro-inflammatory response: implication of Notch signaling in atherosclerosis." Atherosclerosis (2012); 225.2: 296-303.

Liu, Zhao-Jun, et al. "Notch1 signaling promotes primary melanoma progression by activating mitogen-activated protein kinase/phosphatidylinositol 3-kinase-Akt pathways and up-regulating N-cadherin expression." Cancer Research (2006); 66.8: 4182-4190.

Mikhail et al., "Dendrimer-Grafted Cell Adhesion Peptide-Modified PDMS," Biotechnol. Prog. 24:938-944 (2008).

Mulligan, Michael S., et al. "Endothelial targeting and enhanced antiinflammatory effects of complement inhibitors possessing sialyl Lewisx moieties." The Journal of Immunology (1999); 162.8: 4952-4959.

Myung et al., Dendrimer-Mediated Multivalent Binding for the Enhanced Capture of Tumor Cells, Angew. Chem. Int. Ed. 50:11769-11772 (2011) and supporting information.

Oh, Il-Young, et al. "Involvement of E-selectin in recruitment of endothelial progenitor cells and angiogenesis in ischemic muscle." Blood (2007); 110.12: 3891-3899.

Shao, H., et al. "Activation of Notch1 signaling in stromal fibroblasts inhibits melanoma growth by upregulating WISP-1." Oncogene (2011); 30.42: 4316-4326.

Song, Xiaohua, et al. "Will periodic intravenous injections of conditioned bone marrow cells effectively reduce atherosclerosis?." Antioxidants & Redox Signaling (2012); 16.1: 85-91.

Svenson et al. "Dendrimers in biomedical applications—reflections on the field." Adv. Drug. Deliv. Rev. (2005); 57: 2106-2129.

Written Opinion of the International Searching Authority, PCT appl. No. PCT/US2013/042071, 4 pages (dated Oct. 21, 2013).

* cited by examiner

A

B

A

B

C

A Ac-G5-BSA-coated BMC

Ac-G5-sE-sel-coated BMC

B

C

A

B

A

B

DENDRIMER CONJUGATES FOR COATING CELLS

CROSS-REFERENCE TO RELATED APPLICATIONS

This application is a continuation of U.S. application Ser. No. 14/403,107, filed Nov. 21, 2014, which is a U.S. national stage application of PCT Application No. PCT/US2013/042071, filed May 21, 2013, which claims priority to and the benefit of U.S. Provisional Application No. 61/649,607, filed May 21, 2012, in which the disclosure of each is hereby incorporated by reference in its entirety.

FIELD OF THE INVENTION

The present invention relates generally to dendrimer conjugates and uses thereof, including compositions comprising dendrimer conjugates, and using the conjugates for diagnostic or therapeutic purposes. In particular, the present invention relates to a dendrimer conjugate, e.g. a dendrimer conjugated to a cell adhesion molecule (CAM), that coat cells thereby homing the cells to a targeted tissue.

BACKGROUND

Targeted delivery of cells, such as the targeting of therapeutic cells to the endothelium of dysfunctional tissues, remains a formidable challenge. Systemic delivery of therapeutic cells can be accomplished through the circulatory system. Luminal endothelial cells (ECs) form a natural barrier between the blood and surrounding tissue. Under steady-state physiological conditions, luminal ECs are mostly quiescent and form a tight and impermeable barrier. During various pathological processes, such as tissue injury, inflammation, atherosclerosis and tumor, soluble factors such as, SDF-1α, TGF-β, and IL-1, are released into tissue, and the endothelium is stimulated by these factors and switch to a highly permeable status wherein circulating cells, including bone marrow-derived endothelial progenitor cells (EPC), mesenchymal stem cells (MSC) as well as inflammatory cells (IC), are able to infiltrate into the pathologically disrupted tissues. However, infiltration of cells into disordered tissues is not a passive process.

Recruitment of circulating cells into a tissue involves an active and well-modulated circulating cell for EC interaction, and subsequent circulating cell transendothelial migration. Upregulated E-selectin on luminal EC at injured or tumor tissue is believed to be responsible for mediating EPC homing. (Oh, I. Y. et al., *Blood* 110, 3891-3899 (2007); Liu, Z. J. et al., *Ann Surg* 252, 625-634 (2010); Liu, Z. J. et al., *Ann. Surg.* 254, 450-456; discussion 456-457 (2011)). When EPC circulate through the disrupted tissues, the EPC adhere to the E-selectin on the EC surface of capillaries, a process that is followed by subsequent transendothelial migration and extravasation of the EPC. In this sequence of events, adhesion molecule pairs expressed on luminal EC and circulating cells, such as E-selectin and E-selectin ligands, play a pivotal role in directing the selective and specific homing of circulating cells to damaged tissues.

An appropriate adhesion molecule can be utilized to direct cell homing to where a corresponding binding partner is highly or selectively expressed on the luminal EC within the targeted tissue. Thus, by attaching the proper adhesion molecule(s) on the surface of a cell, such as a therapeutic stem or progenitor cells being used for cell-based regenerative medicine therapies, the cell can be directed to a tissue of interest. However, attaching one or more proper adhesion molecule(s) on the cell surface via a biological approach, such as gene expression, has notable disadvantages, as gene expression may bring about downstream secondary effects that can raise safety concerns or lead to unwanted side-effects. For instance, certain highly or newly expressed molecule(s) or even some non-coding sequences in vectors utilized for gene expression manipulation, may affect cell differentiation, which raises the concern for the ultimate fate of the stem or progenitor cells being used for cell-based regenerative medicine therapies.

Accordingly, there is a need for compositions and methods for targeting a cell to a tissue. The present invention meets this need and provides related advantages.

SUMMARY OF THE INVENTION

The present invention provides a dendrimer conjugate and uses thereof. In one embodiment, the conjugate comprises a dendrimer conjugated to a cell adhesion molecule (CAM). The cell adhesion molecule can be an immunoglobulin superfamily CAM (IgSF CAM), addressin, integrin, cadherin or selectin, wherein the selectin can be E-selectin, L-selectin, or P-selectin.

In one aspect of the invention, the dendrimer is a poly (amidoamine) (PAMAM) dendrimer, such as a PAMAM dendrimer of generation 2 to 10. In some embodiments, the cell adhesion molecule is conjugated to the dendrimer by an acetyl group. In yet other embodiments, the conjugate further comprises a growth factor conjugated to the dendrimer, wherein the growth factor can be VEGF.

Also provided herein is a composition comprising a conjugate disclosed herein and a cell, such as a therapeutic cell. In some embodiments, the cell is a progenitor cell or stem cell. The progenitor cell can be an endothelial progenitor cell and the stem cell can be a mesenchymal stem cell. In some embodiments, the cell is an epidermal cell. In yet other embodiments, the cell is a dermal skin substitute cell. The cell can also be a dendritic cell or macrophage. The cell can be in vivo or ex vivo. The cell can be coated with a conjugate disclosed herein ex vivo. In some embodiments, the composition further comprises a pharmaceutically acceptable carrier. The composition can be a powder, gel, matrix, or liquid, and/or a component of a salve, an ointment, an aerosol, a bandage, a transdermal patch, a wound dressing, a cosmetic, or a bioadhesive.

The present invention also provides a method of producing a conjugate disclosed herein, wherein the method comprises: a) acetylating the dendrimer; and b) conjugating the cell adhesion molecule to the dendrimer through an acetyl group of the dendrimer.

Another aspect of the present invention is a method of using a dendrimer conjugate as disclosed herein. In one embodiment, a method of promoting wound healing, tissue repair, and/or angiogenesis in a subject is provided herein. The method can comprise administered to a subject in need thereof a conjugate or composition disclosed herein. The subject can be a human. The subject can have diabetes, peripheral vascular disease, coronary artery disease, radiation dermatitis wound, traumatic wound, or burn wound. The conjugate or composition can be administered intravenously, subcutaneously, intraperitoneally, or topically.

Also provided herein is a method of detecting a progenitor cell comprising: a) administering to a subject a composition comprising a conjugate disclosed herein, wherein the conjugate binds the progenitor cell; and b) detecting the progenitor cell.

Other aspects and embodiments of the invention will be apparent from the following detailed description of the present invention.

DETAILED DESCRIPTION OF THE INVENTION

The present invention provides dendrimer conjugates and uses thereof, including compositions comprising dendrimer conjugates, and using the conjugates for diagnostic or therapeutic purposes. In particular, the present invention relates to dendrimer conjugates that coat cells, such as therapeutic cells, in which the dendrimer conjugate targets and delivers the therapeutic cell to a target cell or tissue.

Figure 1:
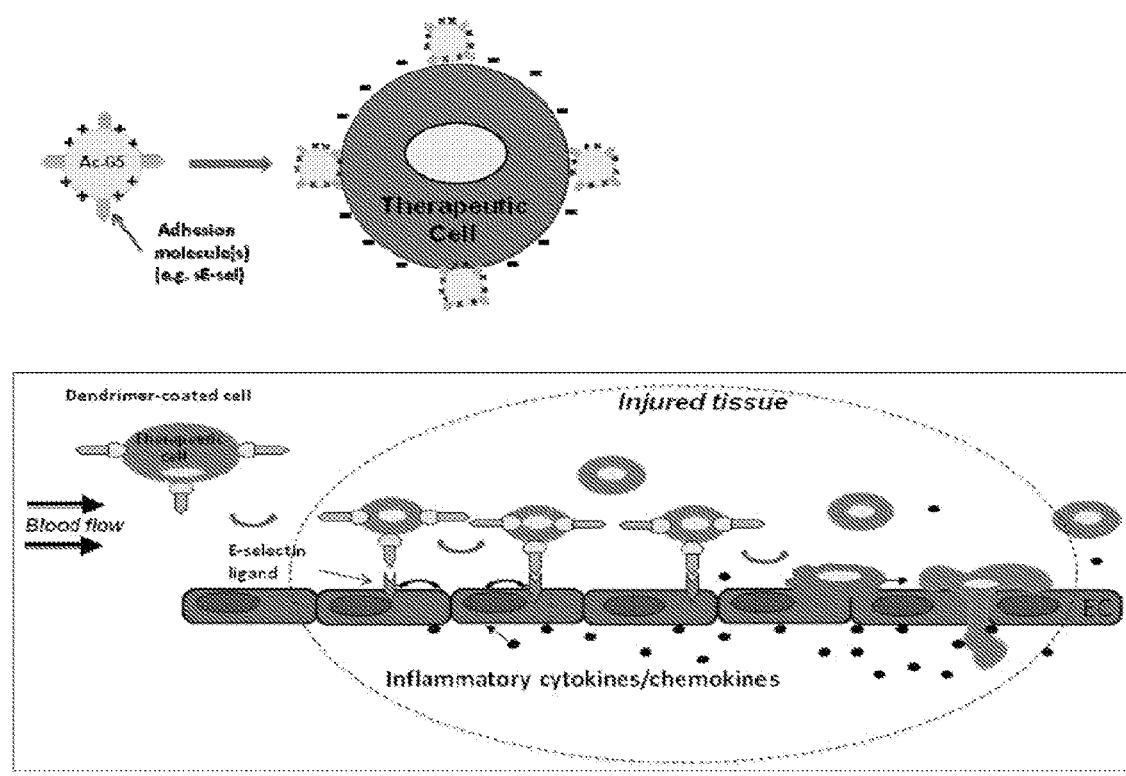
FIG. 1. Schematic illustration of an illustrative cell delivery system. Cell adhesion molecules, e.g. E-selectin (sE-sel), are conjugated to a dendrimer, e.g. Ac-G5 dendrimer, by positive-negative charge interactions and then incubated with cells to be delivered to coat the cell and guide specific delivery to targeted endothelium that is expressing high levels of E-selectin ligand.

The dendrimer conjugates can comprise a dendrimer conjugated to a cell adhesion molecule (CAM), e.g. E-selectin (sE-sel). The dendrimer conjugate can then incubated with cells to be delivered to coat the cell and guide specific delivery of the cell to targeted endothelium that is expressing high levels of E-selectin ligand (see for example, FIG. 1). The dendrimer conjugate can also be used to decorate or coat a cell, such as via in vivo direct particle application to affected tissues, thereby serving as potentially stationary homing 'magnets' to the naturally existing circulating pro-repair cells. The dendrimer conjugate can also be used to detect a cell, i.e. a cell coated or decorated with the dendrimer conjugate.

This novel approach lends itself to broad and versatile application by varying the specific adhesion molecule or peptide loaded on the dendrimer and by choosing the desired cell type to be coated and delivered as payload. For example, potentially therapeutic cells, which are pre-engineered to carry anti-tumor or anti-angiogenic gene(s) or agent(s) may be directed to tumor tissues by coating the cells with a dendrimer, such as Ac-G5-sE-sel dendrimer (acetylated G5-PAMAM dendrimer conjugated to E-selectin) or a similarly constructed variation using oligosaccharide SLEx (Mulligan, M. S. et al., *J. Immunol.* 162, 4952-4959 (1999); Kawamura, N. et al., *Biochem. Biophys. Res. Commun.* 217, 1208-1215 (1995)), since E-selectin is known to be highly expressed in tumor vasculature due to stimulation of SDF-1α generated by tumor stroma (Liu, Z. J. et al., *Ann. Surg.* 254, 450-456; discussion 456-457 (2011)). In addition, direct adherence of repair-competent cells, such as endothelial progenitor cells (EPC) or mesenchymal stem cells (MSC), to areas of vascular injury is one potential approach for arterial repair in the common manifestations of the most widely spread human disease, atherosclerosis (Goldschmidt-Clermont, P. J. et al., *Curr. Opin. Mol. Ther.* 12, 712-723 (2010); Goldschmidt-Clermont, P. J., Dong, C., Seo, D. M. & Velazquez, O. C., *Curr. Atheroscler. Rep.* 14, 201-210 (2012)).

Dendrimers are highly branched macromolecules and can be made from branched monomers through the iterative organic synthesis of adding one layer (i.e., generation) at each step to provide a symmetrical structure. The solution conformation of higher generation dendrimers may closely mimic the size and shape of a protein. Dendrimers can have favorable characteristics, such as structural integrity, control of component functional groups and their physical properties by chemical synthesis, feasibility to conjugate multiple functional units at the peripheries and interiors, and a low enzymatic degradation rate.

Dendrimers have a core from which dendrons branch from. The core molecule is referred to as "generation 0." Each successive repeat unit along all branches forms the next generation, "generation 1," "generation 2," and so on until the terminating generation. The dendrimer of the present invention can be of any suitable generation, e.g., from 2 to 10 or more, such as generation 2, 3, 4, 5, 6, 7, 8, 9, or 10 or more. In some embodiments, the dendrimer may be of a fractional generation, such as 2, 2.5, 3, 3.5, 4, 4.5, 5, 5.5, 6, 6.5, 7, or 7.5. For example, the half generations are carboxyl terminated and full generations are amine terminated. The dendrimer can be anionic or cationic. The conjugate of the invention can include any suitable dendrimer, such as a poly(amidoamine) (PAMAM) dendrimer.

A PAMAM dendrimer typically includes two main components, a branched polymer central initiator core with amine groups for poly(amino acid) attachment, and one or more poly(amino acid) chains, which are directly attached to and which grow from the amine groups of the central initiator core. Table 1 shows the theoretical properties, as determined by Dendritech, Inc., of amine surface functional PAMAM dendrimers by generation:

TABLE 1

| Generation | Molecular Weight | Measured Diameter (Å) | Surface Groups |
|---|---|---|---|
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

The branched polymer central initiator core may include a dendritic polymer or oligomer whose primary function is to define the shape of the dendritic poly(aminoacid) and the number of poly(amino acid) chains attached to the core. The poly(amino acid) chains contain both terminal and side-chain functional groups. The side chain functional groups provide multiple points of attachment for an agent, such as a nucleic acid, protein or peptide, or compound. The agent can be a therapeutic agent, diagnostic agent, or targeting agent (e.g. targeting the dendrimer to a protein, tissue or cell).

The agents may be attached to the functional groups on the poly(amino acid) chains by covalent bonds or ionic interactions. The multiple terminal functional groups on the termini of poly(amino acids) chains which may be different from the side chain functional groups, provide points of attachment for multiple targeting units such as peptides, proteins, monoclonal antibodies etc. that guide the entire construct to the target site. In certain embodiments, the terminal sites are used for attaching a CAM. In other embodiments, different molecules are attached to the terminal sites of a dendrimer, such as a CAM and a therapeutic or diagnostic agent.

In certain embodiments, the central initiator core of the PAMAM dendrimer may be any branched polymer, including dendritic polymer or branched oligomers. These molecules may contain more than two functional groups that may initiate the ring-opening polymerization of the N-carboxyanhydride of amino acids. An exemplary branched polymer is the synthetic polycation, poly(ethylenamine) (PEI). PEI possesses a high number of amine functional groups including primary, secondary, and tertiary amines. These amine groups may serve as points of operative attachment for poly(amino acid) chains. Linear or branched poly(lysine) having multiple primary amines may also be used as initiator. Another example is branched oligomeric lysine.

In other embodiments, the branched polymer may include a dendrimer polycation. Dendrimers are polymers with branched structures arising from concentric layers of polymerized materials with each branch ending in a functional group used for the synthesis of the succeeding generation. Each end group may react with additional monomeric units, resulting in the geometric growth of the molecular size of the polymer and the number of functional end groups. As the generations increase the morphological structure becomes spherical with functional end groups forming a shell on the surface. Dendrimer polycations and methods of preparing them are described in PCT/US83/02052; U.S. Pat. Nos. 6,113,946, 4,507,466, 4,558,120, 4,568,737, 4,587,329, 4,631,337, 4,694,064, 4,713,975, 4,737,550, 4,871,779 and 4,857,599, and can also be purchased commercially. Dendrimer polycations generally comprise oligomeric and/or polymeric compounds attached to a core molecule. As used herein "attached" may include, but is not limited to such attachments as a covalent bond or ionic bond.

Examples of branched polymers as a central initiator core include, but are not limited to, poly(amidoamines) (PAMAM). The typical molecular weights of PAMAM can vary, such as from 359 to 175,000 or more (for ammonia core) and from 517 to 233,000 or more (for ethylenediamine core). The number of amino functional groups can also vary, and can range from 3 to 1024, or more. PAMAM of higher molecular weight and higher numbers of amino groups may also be used to prepare dendritic poly(amino acids).

Another example of branched polymer central initiator cores than can be used to prepare dendritic poly(amino acids) of the present invention include polypropylenimine tetraamine dendrimers (available from Aldrich-Sigma Chemicals, Inc.) such as DAB-Am-4, DAB-Am-8, DAB-Am-16, DAB-Am-32, DAB-Am-64 etc that have 4, 8, 16, 32, and 64 terminal amino groups, respectively.

Poly(amino acids) dendrimers can provide numerous advantages for coating of a cell, in that terminal functional groups may serve as points of attachment for targeting or homing molecules such as CAMs. It is possible to significantly enhance binding affinity through a multivalency cluster effect by conjugating multiple target-homing molecules to dendritic polymeric carriers. Furthermore, with numerous terminal functional groups, multiple agents, such as a CAM and a molecule that promotes wound healing, tissue repair or angiogenesis, can be attached to the dendrimer. In other embodiments, a CAM and a diagnostic agent is attached to the dendrimer. In yet other embodiments, a CAM, a molecule that promotes wound healing, tissue repair or angiogenesis, and a diagnostic agent are attached to a dendrimer.

In certain embodiments, poly(amino acid) chains attached to the central initiator core may include monomers of glycine, alanine, valine, leucine, isoleucine, methionine, proline, phenylalanine, trytophan, asparagine, glutamine, serine, threonine, aspartic acid, glutamic acid, tryosine, cysteine, lysine, arginine, histidine, or combination thereof. The number of monomers in an individual poly(amino acid) chain may be about 3, about 10, about 25, about. 50, about 75, about 100, about 200, about 300, about 400, about 500, about 600, about 700, about 800, about 900, about 1000, or more. The number of monomers in an individual poly(amino acid) chain may also be any integer derivable therein and any range derivable therein. In various aspects, mixtures of poly(amino acid) chains of different lengths may be used. In other embodiments, the number of side-chain functional groups on a particular poly(amino acid) chain may be about 3, about 10, about 25, about 50, about 75, about 100, about 200, about 300, about 400, about 500, about 600, about 700, about 800, about 900, about 1000, and any integer derivable therein and any range derivable therein.

The terminal functional groups on the surface of some nonlinear poly(amino acids) may be primary amines ($—NH_2$). They may be coupled to a homing molecule, such as a CAM, through a variety of $—NH_2$ reactive groups. Alternatively, $—NH_2$ may be further converted to other functional groups such as sulthydryl (—SH), carboxyl (—COOH), maleiimide, vinyl sulfone, aldehyde (—CHO), isothiocyanatobenzyl group (—SCN) etc. with or without the use of spacers. In one embodiment, the $—NH_2$ is functionalized by acetylation. The functional group can then be coupled to a homing molecule, such as a CAM. Dendrimers that are acetylated, such as Ac-G5 dendrimers, can display well tolerated low cytotoxicity. After achieving the desired biologic response, the dendrimer component can be taken up by cells, discharged/expelled from cells and removed from body ultimately via the urinary system, and thus is generally believed to be a non-toxic, "biodegradable" nonoparticle (Boyd, B. J. et al., *Mol. Pharm.* 3, 614-627 (2006).

In some embodiments, the dendrimer is conjugated to at least one targeting molecule directed to a cell, tissue, or organ, such as a CAM. The targeting molecule can be operatively attached or conjugated to the poly(amino acid) chains of a PAMAM dendrimer. In certain embodiments, the targeting ligand is conjugated to the terminal functional groups present on the poly(amino acid) chains. The terminal functional groups, $—NH_2$, —COOH, —SH, vinyl sulfonyl etc. are different from the core functional groups of the dendritic poly(amino acids) and may thus be site-selectively modified to conjugate multiple targeting units. In one embodiment, the terminal function group is an acetyl group. Thus, also provided herein is a method of producing a dendrimer conjugate acetylating the dendrimer; and conjugating a targeting molecule, such as a CAM, to the dendrimer through an acetyl group of the dendrimer.

The dendrimer conjugate can comprise a ratio of dendrimer to targeting molecule ranging from 10:1 to 1:1000, such as about 5:1, 10:3, 5:2, 2:1, 1:1, 1:2, 1:3, 1:4, 1:5, 1:6, 1:7, 1:8, 1:9, 1:10, 1:25, 1:50, 1:100, 1:250, 1:500, or 1:1000. In some embodiments, the ratio is less than 1:5.

When selecting a CAM for being conjugated with a dendrimer, such as to create a dendrimer conjugate to coat a cell, a counterpart receptor/ligand that is not expressed in the cells to be coated may be selected to avoid the formation of cell aggregates formed by cell-cell adhesion, which is likely to affect the efficacy of cell delivery through the circulation. Moreover, to avoid interaction of ligand/receptor induced pro-inflammatory response or other unwanted downstream signal transduction in luminal EC of targeted tissues, a small portion of the CAM which retains binding capacity yet does not fully induce receptor-initiated downstream signaling on the luminal EC, such as the LFA-1 I domain, can be used. Such considerations can decrease potential side-effects.

In some embodiments, the cell to be coated with a dendrimer conjugate expresses the counterpart to a CAM conjugated to dendrimer (such as a ligand specific to the CAM). The CAM ligand expression on a cell can be induced by factors, such as a cytokine or growth factor, such as SDFα-1, TGF-β, or IL-1. In other embodiments, the ligand for the CAM is expressed in the cell by gene therapy. Yet in other embodiments, the ligand for the CAM is delivered to the target cell by delivering to the cell an expression vector encoding the ligand. For example, an expression vector encoding a ligand for the CAM is delivered to the cell, in which the cell expresses the ligand prior to being coated with a dendrimer conjugate with the CAM.

A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention. In one embodiment, an expression vector for expressing a ligand for a CAM comprises a promoter operably linked to a polynucleotide encoding the ligand. The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol 1, pol 11, pol III, and viral promoters (e.g. human cytomegalovirus (CMV) immediate early gene promoter, the SV40 early promoter, and the Rous sarcoma virus long terminal repeat). In one embodiment, the promoter is a tissue-specific promoter, such as for a tissue in which wound healing, repair, or angiogenesis is needed.

In certain embodiments, the promoter operably linked to a polynucleotide encoding a ligand for a CAM can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR. In some embodiments, the promoter is induced by a factor, such as a cytokine or growth factor, such as SDFα-1, TGF-β, or IL-1.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The CAM conjugated to a dendrimer can be a calcium-independent or calcium-dependent CAM. The CAM can be an immunoglobulin superfamily CAM (IgSF CAM), addressin, integrin, cadherin or selectin. IgSF CAMs bind integrins, and in some embodiments, the IgSF CAM is Neural Cell Adhesion Molecule (NCAM) or Intercellular Adehsion Molecule I (ICAM-1). In some embodiments, the CAM is mucosal vascular addressin cell adhesion molecule 1 (MAd-CAM-1), CD34 or GLYCAM1. In some embodiments, the CAM is E-selectin, L-selectin, or P-selectin. In some embodiments, a conjugate comprises a dendrimer conjugated to a CAM, such as E-selectin. In other embodiments, the CAM is vascular endothelial cell adhesion molecule-1 (VCAM-1) or epithelial cell adhesion molecule (EpCAM). In other embodiments, the CAM is a CAM expressed specifically, or overexpressed, by cancer cells. The dendrimer conjugate can comprise a ratio of dendrimer to CAM ranging from 10:1 to 1:1000, such as about 5:1, 10:3, 5:2, 2:1, 1:1, 1:2, 1:3, 1:4, 1:5, 1:6, 1:7, 1:8, 1:9, 1:10, 1:25, 1:50, 1:100, 1:250, 1:500, or 1:1000. In some embodiments, the ratio is less than 1:5.

In some embodiments, the dendrimer is conjugated to a CAM and another agent, such as an agent that reduces the injury or disease state of a cell or tissue to which the dendrimer is targeted to. For example, the dendrimer can be conjugated to a CAM and an agent that promotes wound healing, tissue repair, or angiogenesis. In one embodiment, the agent is a growth factor, such as VEGF. In some embodiments, a conjugate comprises a dendrimer conjugated to a CAM, such as E-selectin, and a growth factor, such as VEGF. The dendrimer conjugate can comprise a ratio of dendrimer to "payload" (i.e. CAM and another agent, such as VEGF) ranging from 10:1 to 1:1000, such as about 5:1, 10:3, 5:2, 2:1, 1:1, 1:2, 1:3, 1:4, 1:5, 1:6, 1:7, 1:8, 1:9, 1:10, 1:25, 1:50, 1:100, 1:250, 1:500, or 1:1000. In some embodiments, the ratio is less than 1:5.

The dendrimer conjugate of the present invention can contain any suitable degree of loading of the CAM and/or agent, e.g., a degree of loading greater than about 0.1%, about 10%, about 20%, about 30%, about 40%, about 50%, about 60%, about 70%, about 80%, about 90%, or more; or 100% or less, about 95% or less, about 85% or less, about 75% or less, about 65% or less, about 55% or less, about 45% or less, about 35% or less, about 25% or less, about 15% or less, or about 5% or less, for example, about 1% to about 99%, about 10% to about 90%, about 20% to about 80%, about 30% to about 70%, or about 40% to about 60%, of the theoretical capacity of the dendrimer.

Another aspect of the present invention is a composition comprising a dendrimer conjugate described herein. In one embodiment, the composition comprises a dendrimer conjugate and a cell. In some embodiments, the dendrimer is conjugated to a CAM. In some embodiments, the composition comprises a cell coated with dendrimers conjugated to CAM. The coating of the cell can be performed ex vivo. In other embodiments, the composition comprises a cell coated with dendrimers conjugated to CAM and one more additional agent. The one or more additional agent can be an agent that reduces the injury or disease state of a cell or tissue to which the dendrimer is targeted to. For example, the dendrimer can be conjugated to a CAM and an agent that promotes wound healing, tissue repair, or angiogenesis.

The cell can be a cell that aids wound healing, tissue repair and/or angiogenesis. The cell can be a progenitor cell or stem cell. For example, the cell can be an endothelial progenitor cell or mesenchymal stem cell. In other embodiments, the cell is a dendritic cell. For example, the dendritic cell can be an antigen loaded dendritic cell. In other embodiments, the cell is a macrophage, such as a M1 or M2 macrophage. In some embodiments, the cell is an epidermal cell or a dermal skin substitute cell. The dermal skin substitute can be biological or biosynthetic. For example, the dermal skin substitute can be a tissue engineered product that uses human and/or animal cells, or both, in a scaffold of natural or synthetic extracellular matrices. In other embodiments, the dermal skin substitute is a tissue engineered product with both biological and synthetic elements comprising the scaffold or matrix. The dermal skin substitute may be commercially available, such as DermACELL™ and others. In some embodiments, the cell is a pancreatic islet cell.

The composition can comprise a dendrimer conjugate disclosed herein, optionally a cell, and a pharmaceutically acceptable carrier. In some embodiments, the composition comprises a cell coated or covered with dendrimer conjugates and a pharmaceutically acceptable carrier. In some embodiments, the composition can be in the form of a powder, gel, matrix, or liquid. In some embodiments, the composition is a component of a salve, an ointment, an aerosol, a bandage, a transdermal patch, a wound dressing, a cosmetic, or a bioadhesive.

In some embodiments, the composition comprises additional components to aid in delivery of the dendrimer conjugate, or dendrimer conjugate and cell (such as a cell covered or coated with dendrimer conjugates), to a subject, such as for pharmaceutical compositions. Pharmaceutical compositions are prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are hereby incorporated by reference in their entireties.

In some embodiments, the composition comprising a dendrimer conjugate, and optionally a cell (or a cell covered with dendrimer conjugates), is formulated for conventional subcutaneous or intravenous administration, for example, by formulating with appropriate aqueous diluent, including sterile water and normal saline. The pharmaceutical compositions and formulations may employ appropriate salts and buffers. Aqueous compositions of the present invention comprise an effective amount of the composition dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal, or intravenous injection, or by direct injection into target tissue. In other embodiments, administration is by topical administration. The stability and/or potency of the dendrimer conjugates and cells coated or covered with dendrimer conjugates disclosed herein allows for convenient routes of administration, including subcutaneous, intradermal, and intramuscular.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

The present invention also provides a method for delivering a dendrimer conjugate, or cell covered or coated with dendrimer conjugates to a cell, tissue or organ (e.g., as part of a composition or formulation described herein). In some embodiments, the method comprises delivering a dendrimer conjugate, or cell covered or coated with dendrimer conjugates to a cell, tissue or organ (e.g., as part of a composition or formulation described herein) to a subject. The subject can be an animal or mammal, such as a human. The dendrimer conjugate and cell, or cell covered in dendrimer conjugates, may be contacted in vitro or in vivo with a target cell, tissue, or organ.

The methods generally comprises administering a dendrimer conjugate and cell (such as a cell coated or covered with dendrimer conjugates) to a subject. In one embodiment, the method comprises delivering a cell covered or coated with dendrimer conjugates to a subject for promoting wound healing, tissue repair and angiogenesis in the subject. In another embodiment, the method comprises delivering a cell covered or coated with dendrimer conjugates to a subject for treating or preventing the progression of diabetes in a subject. A method for promoting transplantation acceptance comprising delivering a cell covered or coated with dendrimer conjugates to a subject is also provided herein. A method for treating, preventing or inhibiting the growth of a cancer, such as a neoplasm, comprising delivering a cell covered or coated with dendrimer conjugates to a subject is also provided herein. In some embodiments, the method comprises inhibiting neoplasia comprising administering a cell covered or coated with dendrimer conjugates to a subject.

In one embodiment, the subject has diabetes, peripheral vascular disease, or coronary artery disease. In some embodiments, the subject has diabetes and the cell covered or coated with dendrimer conjugates is a pancreatic islet cell.

In another embodiment, the subject has a wound, such as a radiation dermatitis wound, traumatic wound, or burn wound. The administration of the dendrimer conjugate and cell (e.g. cell coated or covered with dendrimer conjugates) can be directly to the wound of the subject, such as topically administration, or applied as a component of a salve, an ointment, an aerosol, a bandage, a transdermal patch, a wound dressing, a cosmetic, or a bioadhesive. Thus, the present invention provides a use of the dendrimer conjugates and cells (such as a cells covered with dendrimer conjugates) and compositions of the present invention for treating such conditions, and for the preparation of medicaments for such treatments.

The compositions and methods disclosed herein can be used for the treatment of burns, skin lesions, skin injuries or skin grafts, diabetic wounds and diabetic ulcers, e.g. diabetic foot ulcer, such as by accelerating healing of the wounds.

In another embodiment, the method comprises administering a dendrimer conjugate and cell (such as a cell coated or covered with dendrimer conjugates) to a subject before or during transplantation. The cell can be a donor cell, such as a cell from the donor of the organ being transplanted into the subject.

In another embodiment, the subject has atherosclerosis. In atherosclerosis, specific CAMs (e.g. ICAM-1) are up-regulated on the inflamed EC overlying the forming plaque lesion in the early phase of atherosclerosis changes, leading to recruitment of leukocytes/monocytes and macrophages and subsequent development of progressing atheromas (Liu, Z. J. et al., *Atherosclerosis* 225, 296-303 (2012)). Pro-repair cells (often derived from the bone marrow (Goldschmidt-Clermont, P. J. et al., *Curr. Opin. Mol. Ther.* 12, 712-723 (2010); Song, X. et al., *Antioxid Redox Signal* 16, 85-91 (2012)), can be decorated or coated (ex vivo) with similarly dendrimers conjugated with LFA-1 I domain, a functional peptide of ICAM-1 ligand. Upon systemic re-injection of these cells, the cells would be specifically directed to the atherosclerotic lesions, whereby a direct or indirect (paracrine) mechanism, could mediate the desired "repair" and prevent progression of atherosclerosis.

In some embodiments, a method for promoting wound healing, tissue repair, or angiogenesis comprises administering a dendrimer conjugate and cell (i.e. a cell covered or coated with dendrimer conjugates) and an additional treatment, such as bone marrow cell releasing therapy or pro-angiogenesis therapy, such as hyperbaric oxygen treatment or administration of VEGF or any other angiogenesis promoter of natural or synthetic origin.

In some embodiments, a method for treating, preventing or inhibiting the growth of a cancer, such as a neoplasm, comprises delivering a cell covered or coated with dendrimer conjugates to a subject. In some embodiments, the method comprises inhibiting neoplasia comprising administering a cell covered or coated with dendrimer conjugates to a subject. In some embodiments, the method comprises inhibiting new blood vessel growth associated with the neoplasm. The cell can be an immune cell, such as a macrophage, dendritic cell, or T-cell. The cell can be an M1 macrophage. In some embodiments, the cell is the subject's cell, or generated from a cell of the subject's. The cell can be loaded with a cancer specific antigen. The antigen can be expressed specifically by cancer cells or overexpressed by cancer cells. The antigen can be expressed by specific cancer cell types. The dendrimer conjugate can target the cell, or cell-based therapy, to the microenvironment of the neoplasia, such as to new blood vessels. In some embodiments, the composition is administered by oral, transdermal, sustained release, controlled release, delayed release, suppository, catheter, or sublingual administration. In some embodiments, such as for promoting the healing or repair of an ocular injury or transplantation, the composition is administered intraocularly, such as by intravitreal injection into the eye, or by subconjunctival or subtenon injection.

In some embodiments, the method comprises administering a composition that induces the expression of a CAM ligand, prior to administering a dendrimer conjugate that covers the cell. In some embodiments, the composition comprises a factor that induces the expression of a CAM ligand, such as a cytokine or growth factor, such as SDFα-1, TGF-β, or IL-1. In other embodiments, the composition induces expression of the CAM ligand, such as a composition comprising an expression vector for the CAM ligand.

In certain embodiments, the dendrimer conjugate and cell (such as a cell covered with dendrimer conjugates) is administered at a dose of 25 mg/kg or less, or a dose of 10 mg/kg or less, or a dose of 5 mg/kg or less. In these embodiments, the dendrimer conjugate and cell (such as a cell covered with dendrimer conjugates) may be administered by intramuscular or subcutaneous injection, or intravenously.

Another aspect of the present invention is a dendrimer conjugate disclosed herein further conjugated to a marker, e.g., a dye or a fluorescent marker, which can allow imaging, such as in vivo imaging, which permits the detection of a diagnostic agent delivered with the a dendrimer conjugate, in which the CAM targets the dendrimer conjugate to a target area located in a subject's body.

Diagnostic agents can be delivered to target regions of a subject for imaging a target area, such as an area exhibiting a disease state, with a dendrimer conjugate disclosed here. In some embodiments, the disease state may be a cancerous tumor or tumor cells. This method involves administering to a subject an imaging-effective amount of a diagnostic agent (i.e. the amount of the detectable-labeled agent administered that is sufficient to enable detection of the agent to the target area) operatively attached to a dendrimer, such as a dendrimer conjugated to a CAM, and detecting the binding of the diagnostic agent to the target area, e.g. a tissue. In some embodiments, the diagnostic agent is to detect a progenitor cell in a subject. The method can comprise a) administering to a subject a composition comprising a dendrimer conjugated to a CAM and a diagnostic agent, wherein the conjugate binds the progenitor cell; and b) detecting the progenitor cell.

The diagnostic agent may be any biocompatible or pharmacologically acceptable agent which may be operatively attached to a dendrimer conjugate of the present invention. In a non-limiting example, the biocompatible or pharmacologically acceptable agent is an imaging agent including the commercially available agents for use in computer assisted tomography (CT), magnetic resonance imaging (MRI), fluoroscopy, near-infrared optical imaging, positron emission tomography, single photon emission computerized tomography, and x-ray. Examples of these agents include iodinated compounds for CT, paramagnetic an superparamagnetic metal ions such as Gd, Mn, Dy, Cr, and Fe for MRI, near-infrared fluorescent probes such as derivatives of indocyanine green for near-infrared optical imaging, and radionuclides for nuclear imaging. Radionuclide or paramagnetic agents may be bound to a dendrimer conjugate with or without spacers and by using chelators.

EXAMPLES

Example 1: Dendrimer Acetylation and Protein Conjugation

To determine the optimal conditions for a dendrimer/protein conjugate to remain on a cell membrane without internalization, various dendrimer/albumin-FITC ratios were tested where the dendrimers used in the conjugate could be unmodified G5 or G3 dendrimers, and acetylated G3 or G5 dendrimer (Ac-G3 or Ac-G5).

The G3 or G5 dendrimer has repeated amidoamine branching on an ethylenediamine core, which can bind well to protein, DNA or saccharides (Gardikis, K., Micha-Screttas, M., Demetzos, C. & Steele, B. R. *Curr. Med. Chem.* 19, 4913-4928 (2012)). The G5 or G3 dendrimer-payload conjugate carries a positive net charge which enables the construct to attach to negatively charged cell membranes. The interaction of the G3 or G5 dendrimer/payload and cell membrane can result in the delivery of the conjugate into cells. Cells vary in their uptake on the dendrimer/payload at varying rates. Mesenchymal stem cells (MSC), for example, showed a high internalization rate with G3 or G5 dendrimers conjugated with albumin-FITC at a range of dendrimer protein ratio of 7:1 to 10:1. The internalization rate is determined by many factors, one important factor being the extent of positive charges.

Acetylation of dendrimers can prolong the cell surface stay of a dendrimer-carrier construct. G5 dendrimers were acetylated at approximately 30% resulting in lowering the level of positively charged amines, which in turn would create a less positively charged conjugate of G5-protein. To acetylate the G5 dendrimers (Ac-G5) for conjugation of a protein with Ac-G5, the ratio between acetic anhydride and the dendrimer was adjusted so that about 20% of the total amine groups would be acetylated. To 15 mL of anhydrous methanol in a magnetically stirred round bottom flask, 1 mL of 5 wt % PAMAM (0.05 g, 1.73 μmol, 1.0 eq) in methanol was added. Triethylamine (6.8 μL, 48.71 μmol, 28.15 eq) was added to the flask and stirred for 30 minutes. Then, acetic anhydride (4.2 μL, 44.29 μmol, 25.6 eq) was added dropwise to the reaction mixture and the reaction was carried out overnight at room temperature under an argon atmosphere. The methanol was then removed by rotary evaporator, and the residue was dissolved in distilled water. The dendrimer solution was then dialyzed against 1 L of PBS for 8 hours followed by extensive dialysis against water (3×8 hours) in a 10 KDa cutoff Slide-ALyzer Dialysis cassette (Pierce Biotechnology, Rockford, Ill.). The samples were then lyophilized and stored at 4° C. Proton nuclear magnetic resonance (1H NMR) spectra were taken in D20 using a Varian 400 MHz spectrophotometer, using the solvent as reference signal. The extent of primary amine acetylation was determined from the NMR data.

The resulting conjugates were co-cultured with mouse bone marrow-derived mesenchymal stem cells (BM-MSC) and the binding locations were assessed using confocal microscopy and scanning electron microscopy.

Cell culture and coating of cells was performed by enriching for mouse MSC by culturing whole BMC with murine MesenCult® (Stem Cell Technologies) in Petridish with a periodical medium changes. All cells were incubated at 37° C. in 98% humidified air containing 5% $CO_2$. To coat cells, $5 \times 10^6$ cells were mixed with dendrimer-protein conjugate suspended in 1 mL PBS for 30 minutes at room temperature with a periodical shaking (every 5 minutes). Cells were applied for individual assay after washing with 3 mL PBS for three times.

Transmission electron microscopy (TEM) and confocal imaging to detect cell surface bound dendrimer-protein conjugate was performed by having the murine MSC cells seeded as subconfluent on 24-well glass bottom plates (P24G-1.5-10-F, MatTek) pre-coated with Poly-L-Lysine and allowed to attach overnight. Dendrimer-protein conjugates of different mole ratios were added to the cells and allowed to incubate for 90 minutes at 37° C. After incubation, the media was gently aspirated and the cells were washed with 500 μL PBS twice. Cells were imaged with a Leica SP5 confocal microscope with HCX Plan APO CS 40.0×1.25 oil UV and HCX Plan APO Lambda Blue 63.0× 1.40 oil UV objective lens and an Argon laser excitation at 488 nm. Z-stacks were 25 μm thick with each slice picture taken at 0.5 μm intervals.

Figure 2:
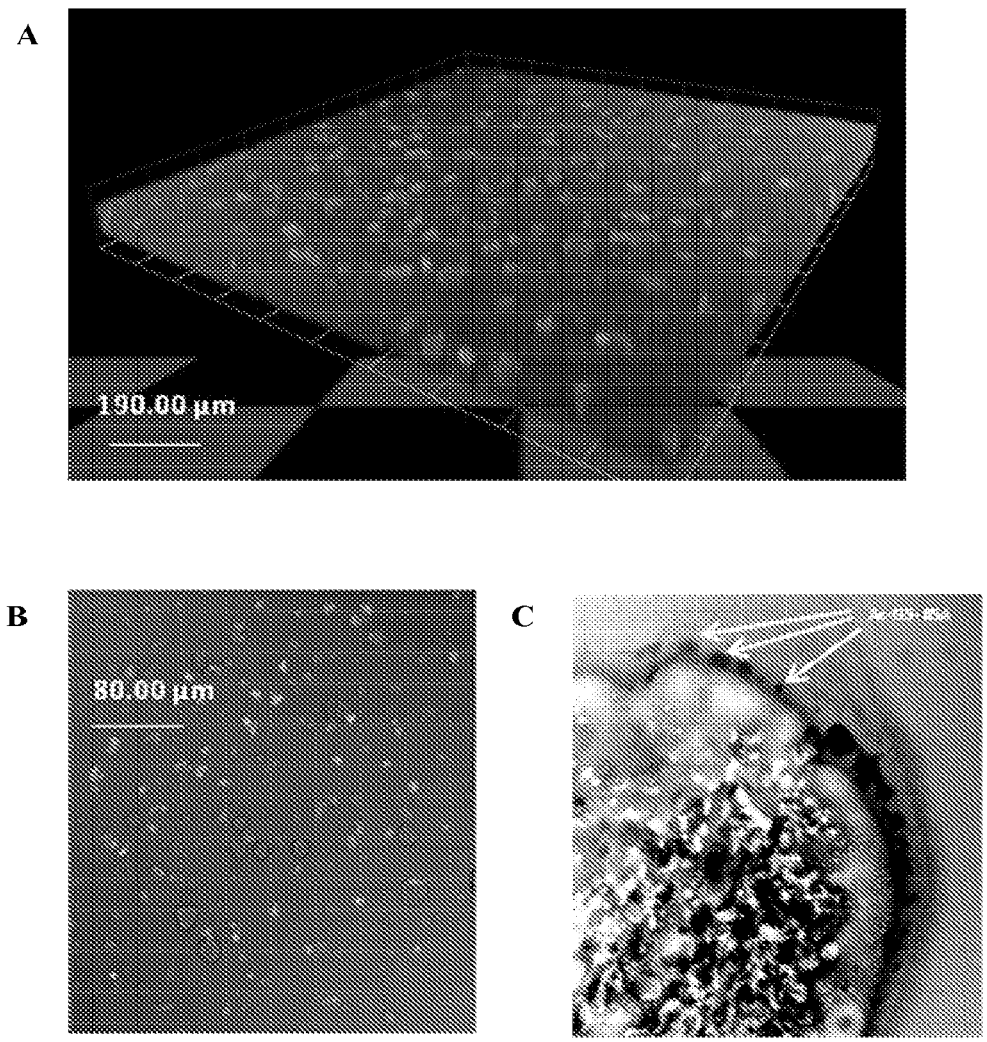
FIG. 2. Sustained stay of Ac-G5-dendrimer-protein conjugate on the cell surface. Murine mesenchymal stem cells (MSC) were coated with albumin-Alexa-488 conjugated to Ac-G5-dendrimers and subjected to image analysis for 2 hours. (A) High resolution orthogonal 3D overview of confocal z-stack imaging of showing Ac-G5-BSA localization at the cell surface of MSC (×40). (B) High-resolution surface confocal imaging of coated MSC (×40). (C) TEM imaging of coated MSC, with arrows pointing to Ac-G5-BSA conjugate.

FIG. 2 shows Ac-G5 dendrimers conjugated with albumin-FITC stayed on the cell surface of BM-MSC for 3 hours with minimal internalization. The acetylation of the G5 is also expected to reduce the cytotoxicity of the dendrimer.

Example 2: Viability of HUVEC Covered with Dendrimer Conjugates

We examined cell viability of human umbilical vein endothelial cells (HUVEC) treated with dendrimers under different conditions using a cell viability assay and cell apoptosis assay by flow cytometry.

HUVEC were purchased from ATCC (PCS-100-010) and human EPC were purchased from NDRI, Philadelphia, Pa., and cultured as described in Liu, Z. J. et al., *Ann Stag* 252, 625-634 (2010). HUVEC were mixed with various conditions of dendrimers or bovine serum albumin (BSA, as control) for 2 hours at 37° C. and dead cells were stained by trypan blue.

Figure 3:
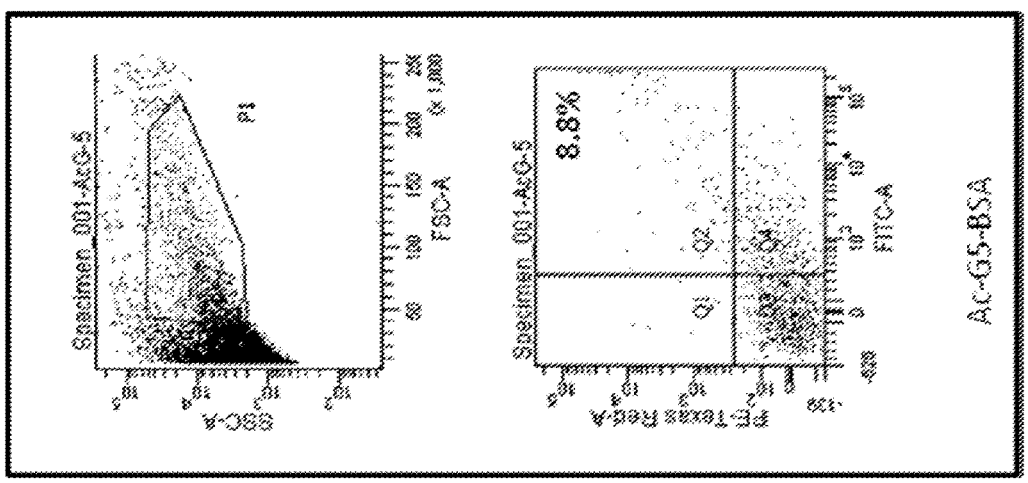
FIG. 3. Toxicity of dendrimers to human endothelia cells under different condition (incubation time with cells: 30 min at room temperature). (A) % of dead cells counted by trypan blue staining Protein: Ac-G5 at ratio 5:1 did not result in cell toxicity. (B) 5:1 ratio was tested by Annexin V-FITC binding using flow cytometry to confirm no/low toxicity to human umbilical vein endothelial cells (HUVEC).
Figure 3:
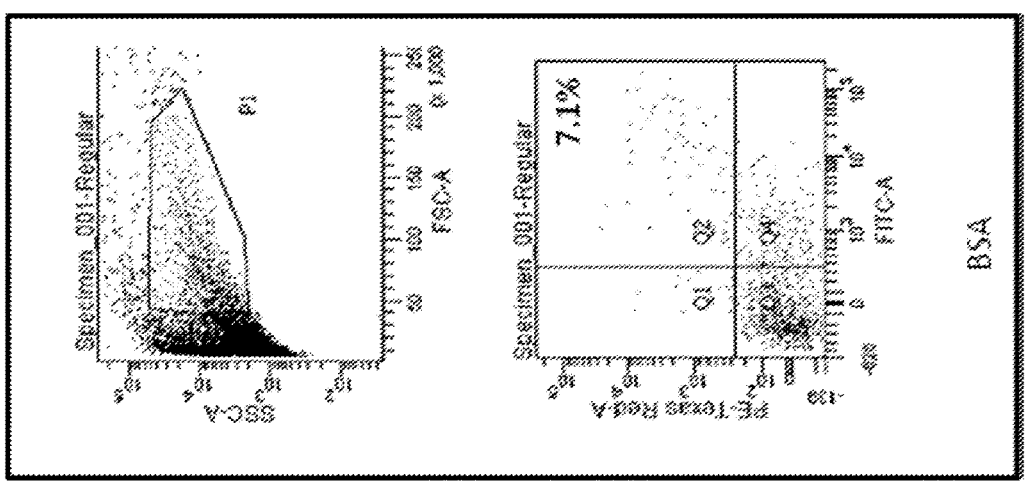

Cell viability was estimated by trypan blue exclusion assay and percentage of dead cells was evaluated by counting blue stained versus total cell numbers using light microscopy. The percentage of dead cells was calculated by counting total cells versus trypan blue uptaken cells. Cell viability assay demonstrated that at under a ratio 1:5 (dendrimer: protein), the Ac-G5 dendrimer did not result in HUVEC cytotoxicity (FIG. 3A).

Cell apoptosis was analyzed by FITCAnnexin-V and propidium iodide (PI) double staining. $1\times10_6$ HUVEC were incubated with BSA-conjugated Ac-G5 or unconjugated Ac-G5 for 2 h at 37° C. Cells were detached and washed with cold PBS. Phosphatidylserine externalization was assessed by Annexin V/PI double staining, according to the manufacturer's instructions (ApoAlert Annexin V-FITC Apoptosis Kit; BD Biosciences). The results were analyzed using a flow cytometry with WinMDi software (Becton Dickinson). Flow cytometric detection of early apoptotic HUVEC using Annexin V-FITC confirmed a negligible cell toxicity index for Ac-G5 dendrimer at ratio 1:5 compared to the BSA treated control (FIG. 3B).

Thus, Example 1 identified the optimal dendrimer conditions for cell surface coating with minimal internalization, and this Example demonstrated that this dendrimer carrier construct is safe to human cells, in vitro.

Example 3: Cell Adhesion with Mono-Arm and Dual-Arm Dendrimer Conjugates

Figure 4:
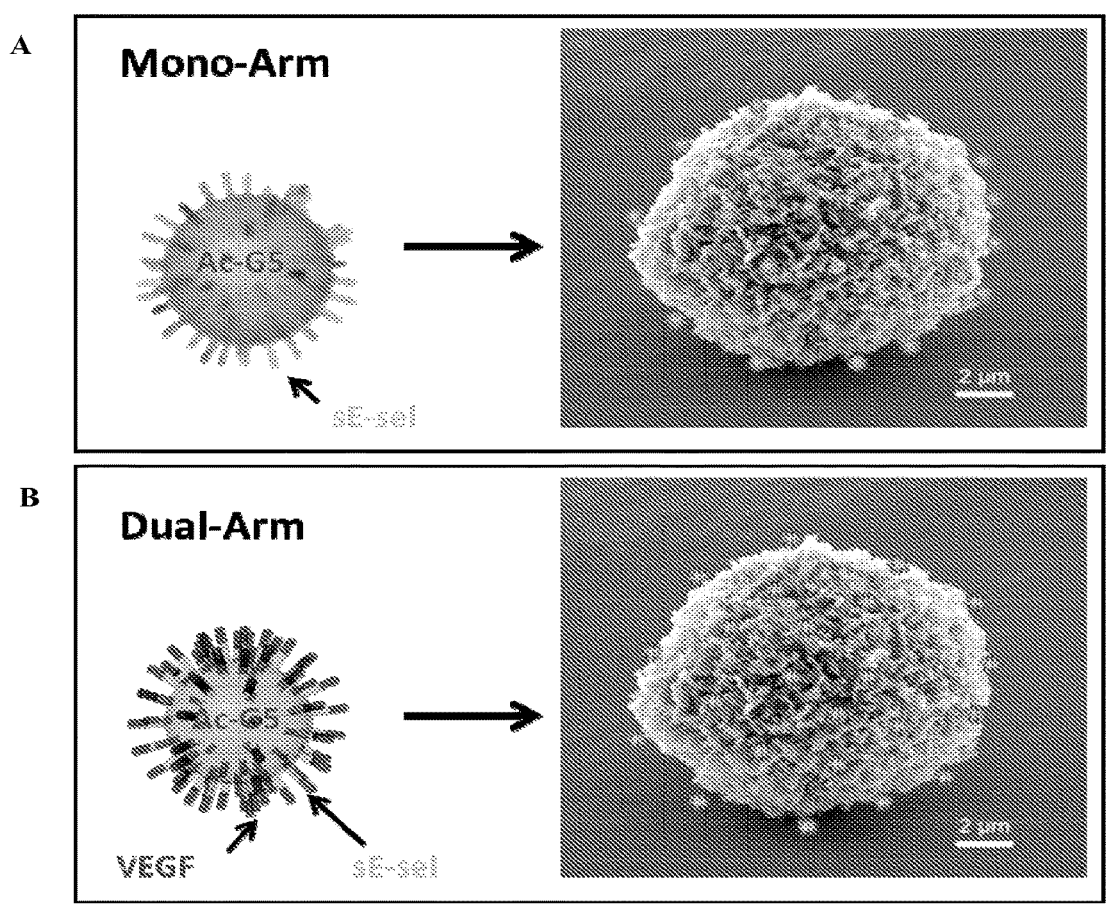
FIG. 4. Coating of cell surface with mono-arm and double-arm dendrimer-protein conjugate. (A) Schematic illustration of "mono-arm" (sE-sel)-dendrimer conjugate for cell coating and image analysis. (B) Schematic illustration of design "double-arm" (sEsel/VEGF)-dendrimer conjugate for cell coating and image analysis.

In vitro cell-cell adhesion experiments were conducted to test the effectiveness of soluble E-selectin (sE-sel) ("mono-arm construct") (FIG. 4A), or sE-sel and VEGF ("double-arm construct") (FIG. 4B) dendrimer-mediated EPC-EC interaction. Mono-arm and dual-arm dendrimer conjugates were produced by reconstituting sE-Sel and VEGF (10335-H08H and 10008-HNAB, Sino Biological Inc., Beijing, China) in sterile water to a final concentration of 0.66 mg/mL and 0.4 mg/mL, respectively. Ac-G5, sE-Sel and VEGF were separately diluted to different concentrations in Opti-MEM Reduced-Serum Medium (Invitrogen, Grand Island, N.Y.) to give different mole ratios of dendrimer: protein ranging from 10:1 to 1:10. The protein was added to Ac-G5 dropwise and with gentle mixing. The mixtures were incubated for 15 minutes at room temperature to allow for conjugateation. Images of the mono-arm and dual-arm dendrimer conjugates are shown in FIG. 4.

The human EPC to be coated with the mono-arm and dual-arm dendrimer conjugates were pre-transduced with DsRed+/lentivirus (DsRed+EPC). DsRed/lenti were constructed as described previously (Liu, Z. J. et al. *Cancer Res.* 66, 4182-4190 (2006); Shao, H. et al. *Oncogene* 30, 4316-4326 (2011)). Production of pseudotyped lentivirus was achieved by co-transfecting 293 T cells with three plasmids as described (Liu, Z. J. et al. *FASEB J.* 20, 1009-1011 (2006)). The lentiviruses collected 48 hours post-transfection displayed titers of around $10_7$ transducing units/ml as determined by PCR. To infect cells by lentiviruses, cells were exposed for six hours to virus with MOI (multiplicity of infection) 5 in the presence of 4 µg/mL polybrene (Sigma-Aldrich). Cells were then washed, cultured with regular complete medium for two additional days, and analyzed by fluorescence microscope. Cells were pooled for subsequent analysis as indicated in individual experiments.

Subconfluent HUVEC ($1\times10^5$ cells/well of HUVEC) were cultured in 24-well glass plates (P24G-1.5-10-F, MatTek) pre-coated with 1% gelatin and cells reached 100% confluence one-day later. The HUVEC monolayers were stimulated with recombinant human SDF-1α (R & D Systems) to induce the E-selectin ligand expression or BSA (control) at 100 ng/ml for 8 hours. Human EPC pre-transduced with DsRed+/lentivirus ($1\times10^5$ DsRed+ EPC), pre-coated with Ac-G5dendrimers carrying a payload of either soluble E-selectin (sE-sel) ("mono-arm construct") (FIG. 4A), or sE-sel and VEGF ("double-arm construct") (FIG. 4B), or BSA, were suspended in 1 mL basal EGM2 medium and co-cultured with HUVEC monolayers for 1 hour.

Figure 5:
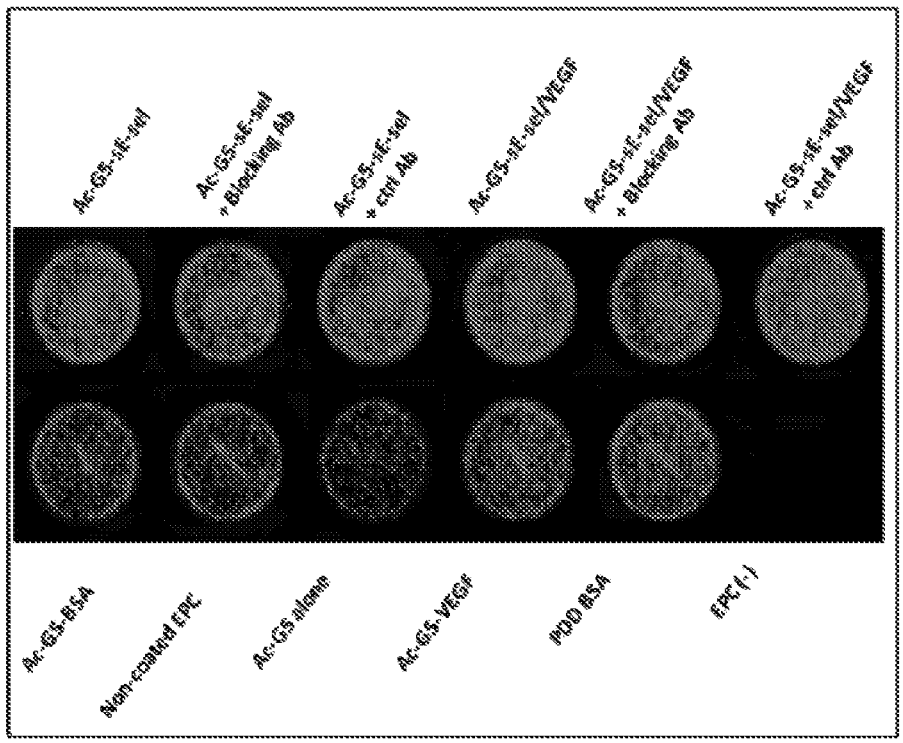
FIG. 5. Coating cell surface with dendrimer-protein conjugate for mediating cell-cell interaction in vitro. In vitro EPC-EC binding assay. "Mono-arm" and "double-arm" DsRad+ EPC displayed an increased binding capability to HUVEC monolayer. E-selectin blocking antibody vs. control antibody were applied to test the specificity of E-selectin in mediating association of EPC-EC. (A) Representative images of DsRed fluorescence in wells. (B) Quantitative data of DsRed fluorescence signals. Data are presented as mean±SD of three independent assays in which samples were duplicated.
Figure 5:
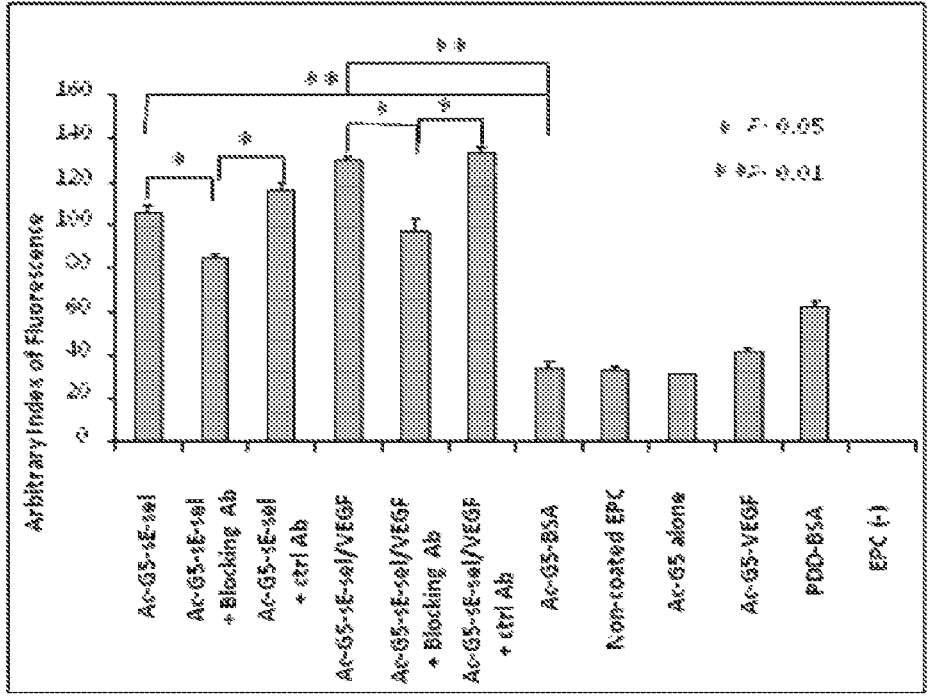

To study whether dendrimer-sE-sel is responsible for mediating enhanced EPC-EC adhesion, the effect of E-selectin antagonist on affecting EPC adhesion to SDF-1α-stimulated EC monolayer in vitro was tested. For this purpose, E-selectin neutralizing antibody (R & D Systems, BBA1) or isotype-matched control antibody (2 µg/ml) were added into EC monolayer and incubated for 15 minutes at 37° C. before adding demdrimers-protein conjugate coated EPC. HUVEC-EPC mixtures were co-cultured for 1 hour at 37° C. Unbounded DsRed+ EPC were washed out twice with PBS. Red fluorescence signals derived from adherent DsRed+ EPC were measured and quantified by fluorescence scanner (GE Typhoon Trio, Piscataway, N.J.) (FIG. 5) and confirmed by fluorescence microscopy (data not shown). Statistical analysis of differences was performed using ANOVA and 2-tail Student's t-test. Data was analyzed using Microsoft Excel (Microsoft Corp, Redmond, Wash.). Data is expressed as mean±standard error. Values are considered statistically significant when $p<0.05$.

DsRed+ EPC coated with Ac-G5 dendrimers carrying sE-sel or the combination of the s-E-sel and VEGF clearly showed superior adhesion to the HUVEC monolayers. Application of E-selectin blocking antibody significantly inhibited this binding of EPC coated with both "mono-arm" and "double-arm" to EC monolayers compared to the control antibody, indicating increased and specific cell-cell interaction that is mediated by the membrane-bound constructs of dendrimer-sE-sel or dendrimer-sE-sel-VEGF. The experiments thus demonstrated the effectiveness of the demdrimers-adhesion molecule constructs in serving as anchors for specific mediating cell-cell interactions.

Example 4: Homing of Ac-G5-sE-sel Conjugate Coated MSC to Murine Wound Tissues To determine whether the membrane-bound dendrimer-protein conjugates described in Example 3 can direct MSC homing to a targeted tissue and result in a desired pro-repair biologic readout, a murine skin wound model was used. All cutaneous wound procedures on mice were done under anesthesia as previously described (Liu, Z. J. et al. *Ann Surg* 252, 625-634 (2010).

The interaction between the delivered mouse MSC and EC of the wound's capillary lining would depend upon mutually relevant counterparts of adhesion molecules on the surface of both cell types. It is known that the wound's capillaries will highly express certain adhesion molecules due to stimulation of inflammatory cytokines/chemokines, such as SDF-1α, IL-1, and TGF-β. The expression of E-selectin ligand, CD44, in the vasculature of wound tissues was determined as the experiment was to test dendrimer-sE-sel conjugate in mediating homing of MSC to wound tissue.

The vessels in the acute skin wounds versus normal skin of C57 BL6 mice were examined by immunochemistry (IHC). Five µm paraffin sections of wound or skin tissues were processed as described (Liu, Z. J. et al. *Ann Surg* 252, 625-634 (2010)) and were incubated with FITC-anti-CD44 (Abcam, ab25340) and PE-anti-KDR (Labome, 136403) for overnight at 4° C. The nuclei were counterstained with either DAPI (Vector Labs, Burlingame, Calif.). Negative controls for all antibodies were made by replacing the primary antibodies with non-immunogen, isotype matched antibodies from the same manufacturer. These experiments confirmed that luminal EC in skin wounds expressed higher CD44 compared to normal skin from the same mouse. Thus, the highly expressed CD44 on the endothelium of capillaries within skin wounds could serve as an excellent model to test the effectiveness of dendrimer-sE-sel coated MSC in homing to the tissue and yielding a pro-repair biologic response.

MSC to be delivered were obtained by culture of BMC from Rosa26(LacZ+) mice in MesenCult® medium for 2 weeks with periodical medium changes. MSC are identified as CD73+/CD105−/STRO-1+, but do not express E-selectin (data not shown). These MSC (LacZ+) were coated by Ac-G5-dendrimer-conjugated with sE-sel versus BSA, in 'treatment' versus 'control cells', respectively.

$1 \times 10^7$ BM-MSC from 1012-week old Rosa26(LacZ+) mice (B6.129 S7-GT (ROSA)26sor/J, Jackson Lab, Stock#002192) were pre-conjugated with Ac-G5-sE-sel or Ac-G5-BSA dendrimers. $1 \times 10^6$ coated cells were transplanted by intravenous tail vein injection into C57BL6 mice (Charles River, strain code: 027) (n=6) on which a 6-mm dorsal cutaneous excisional wound was created 2-hour before by skin biopsy. Wounds were induced on the dorsal surface of the mouse using a 6-mm punch biopsy. Daily wound area measurements were conducted via digital photography. Seven days post wounding, mice were sacrificed and wound tissues were harvested and subjected to IHC. Full-thickness skin was removed, exposing the underlying muscle. Wound healing rates were analyzed as previously described (Liu, Z. J. et al. *Ann Surg* 252, 625-634 (2010); Castilla, D. M. et al. *Ann. Surg.* 256, 560-572 (2012)).

MSC (LacZ+) recruited to wound tissues were detected by x-gal staining (blue). Blood vessels in wound tissues were stained with anti-CD31 antibody. The number of LacZ+ MSC recruited to wound tissues was quantified by β-galactosidase assay (Liu, Z. J. et al. *Ann Surg* 252, 625-634 (2010)). Harvested wound tissues were frozen and tissue sections were then incubated with x-gal (Fermentas, Canada) for 2 hours at room temperature. Sections were counterstained with nuclear fast red (Vector Labs). The number of recruited MSC was quantified by counting β-galactosidase+ cells in serial sections of wound tissues underlying the excisional wounds at post-operative day 7 (n=6) in 5 random high power fields (HPF, 40×) per section in at least 3 serial sections. To stain blood vessels, tissue sections were incubated with HRP-anti-CD31 (Abcam ab28364) or isotype matched control antibody for overnight at 4° C. IHC was conducted as previously described (Liu, Z. J. et al. *Ann Surg* 252, 625-634 (2010); Liu, Z. J. et al. *Ann. Surg.* 254, 450-456; discussion 456-457 (2011)).

Figure 6:
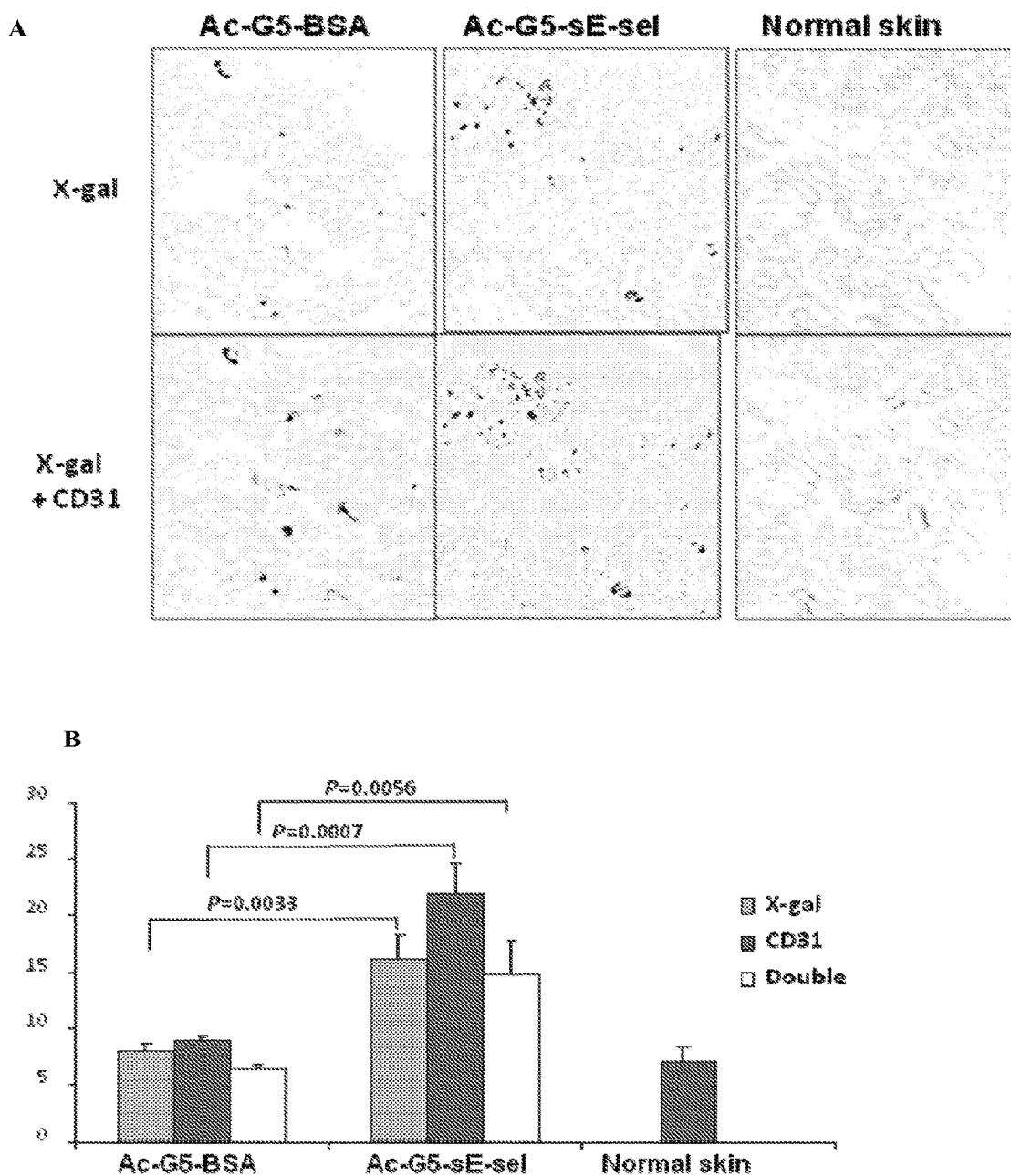
FIG. 6. Contribution of systemically administered MSC to the capillary beds of healing cutaneous wounds. More Ac-G5sE-sel conjugate coated LacZ$^+$ MSC than SA control cells result in an enhanced pro-angiogenic effect of the coated MSC on wound neovascularization, after tail vein injection. Wounds were harvested at day 7 post cell transplantation and frozen samples were subjected for X-gal (blue) staining Normal skin tissues were also harvested as negative control. (A) Representative images of β-gal and CD31 IHC staining of wound and normal skin tissues. (B) Quantitative data of βgal$^+$, CD31$^+$ and β-gal$^+$/CD31$^+$ double positive cells per low power field (×10). Number of β-gal$^+$ cells was counted from 5 randomly selected fields in wound samples. Data are percentage of mean±SD from each group (n=6 mice/group).
Figure 7:
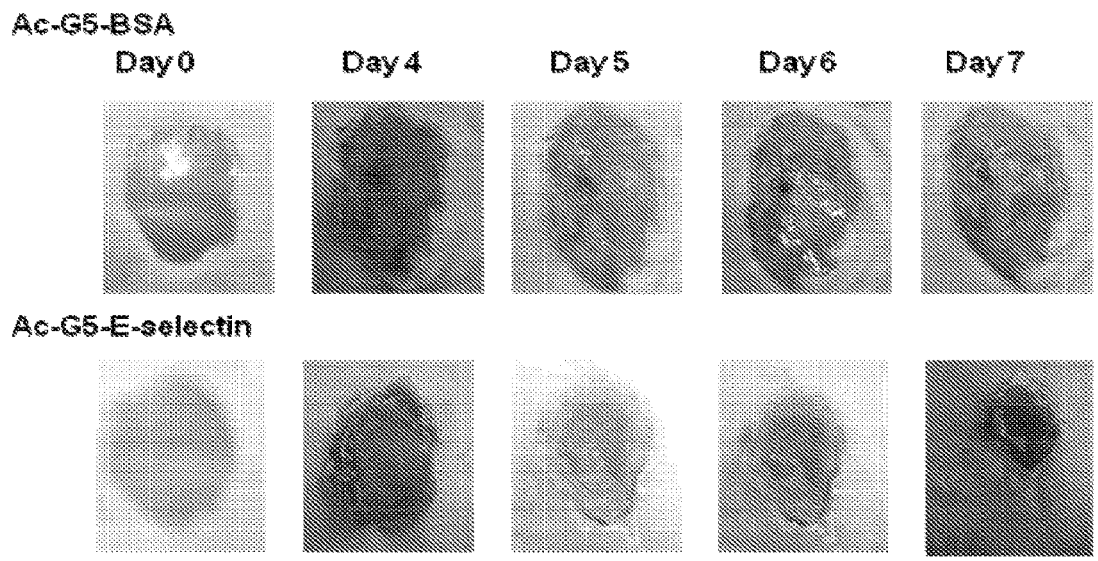
FIG. 7. Pro-healing effect of directed delivery of Ac-G5-sE-sel conjugate coated MSC to murine wound tissues. 1×10$^7$ BM-MSC from 10-12-wk old Rosa 26(LacZ$^+$) mice were pre-conjugated with Ac-G5-sE-sel or Ac-G5-BSA dendrimers and then engrafted (i.v.) into wounded C57/BL6 mice 2-hr after creation of skin wounds. Wounds were induced on the dorsal surface of the mouse using a 6-mm punch biopsy. Wound healing rate expressed as percent recovery. The fraction of initial wound area was measured daily by digital photography and ImageJ analysis until day 7. (A) Representative wounds at different days are shown for each group. (B) Wound healing rate. Data are percentage of mean±SD from each group (n=6 mice/group).
Figure 7:
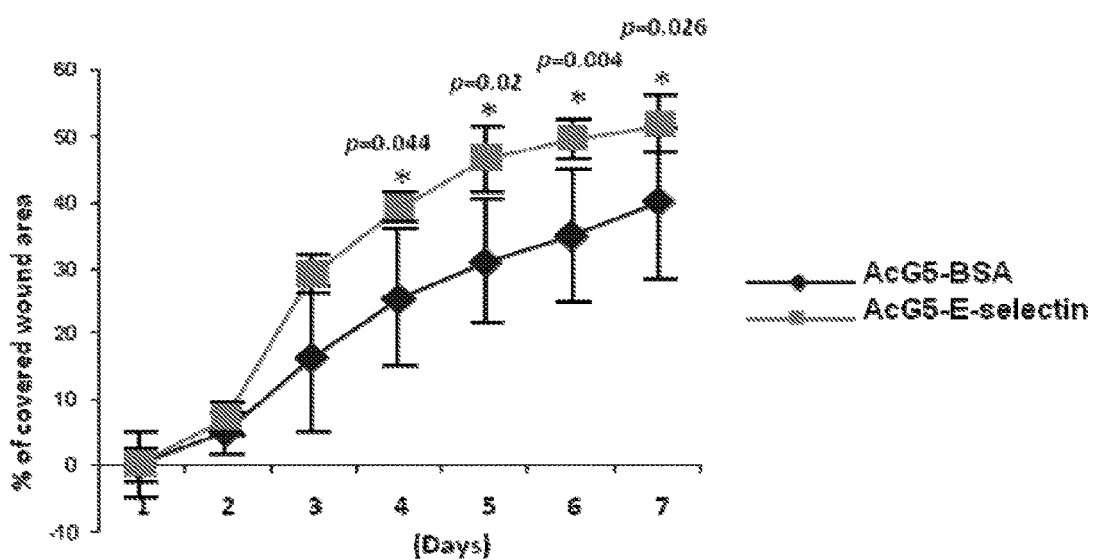

Compared to mice injected with control cells (Ac-G5-BSA MSC), the mice injected with the treatment cells (Ac-G5-sS-sel MSC), showed significantly increased LacZ+ MSC within their cutaneous wound tissues (FIG. 6). Some of these intravenously injected cells not only specifically homed to the wound, but also incorporated into the wound's blood vessels, suggesting that MSC may differentiate into EC or become pericytes. Most importantly, a faster wound healing rate (the intended pro-repair biologic effect for the 'treatment' design in this model) and drastically increased wound vessel density (angiogenesis, an important and distinct biologic readout with treatment implications for many common human diseases such as coronary artery disease and peripheral vascular disease) was observed in mice engrafted with Ac-G5-sE-sel coated MSC compared to control mice infused with Ac-G5-BSA coated MSC (FIG. 7).

It is important to note that, at baseline, C57BL6 heal at normal rates (i.e. this was not a model of delayed wound healing). Thus, the observed acceleration of cutaneous wound healing over baseline is the first demonstration that ex vivo manipulation of pro-repair cells with systemic re-injection of these coated cells can augment the normal healing cascades. This may be a function of increased pro-repair numbers (guided to home to the wound via the Ac-G5-sE-sel dendrimer coat) and/or additional paracrine effects initiated by the MSC-EC direct cell-cell interactions.

Example 5: Homing of Ac-G5-sE-sel Conjugate Coated BMC to Incision Site

To further explore the versatility of this concept of using cells decorated with the Ac-G5-sE-sel dendrimer conjugates for specific cell delivery to tissues undergoing repair, an in vivo model of cornea transplantation was used. In these experiments, freshly isolated bone marrow-derived mononuclear cells (BMC) without any ex vivo expansion or any specific EPC or MSC enrichment was used. The role of Ac-G5-sE-sel in recruitment of BMC into grafted corneas was studied using a syngeneic corneal transplantation model known to induce neovascularization.

Mice were anesthetized with Ketamine (100 mg/kg) and Xylazine (10 mg/kg) intraperitoneally (i.p.) before the surgical procedure. Orthotopic corneal transplantations were performed with EGFP+ transgenic mice as donors and C57BL/6 as recipients for syngeneic grafts as previously describe 16. Initially, a central 2-mm full thickness trephination of the recipient cornea was performed followed by excision with corneal scissors. Corneas from donor mice were then prepared in a similar fashion and secured to the recipient bed using eight interrupted 11-0 nylon sutures (Sharppoint, Tex.). Erythromycin ointment was applied and transplants were examined 72 hours after surgery. Corneal grafts with flat anterior chamber, ulceration or other complications related to surgical difficulties were excluded. All corneal sutures were removed at post operation day (POD) 7.

BMC from EGFP transgenic mice were conjugated with either Ac-G5-sE-sel or Ac-G5-BSA. On the day 14 POD, $1 \times 10^6$ BMC coupled with either Ac-G5-BSA or Ac-G5-sE-sel were injected in mice d via tail vein into corneal graft recipients, (n=5/group). The next day, the corneas of mice (under isoflurane (2%) anesthesia) were imaged using an in vivo, live confocal fluorescent microscope.

Corneal grafts were imaged longitudinally as previously described (Abdulreda, M. H. et al. *Proc. Natl. Acad. Sci. USA* 108, 12863-12868 (2011)). Briefly, mice were anesthetized with an air/isoflurane mixture delivered through a custom-built mask incorporated in a stereotaxic holder (SG-4N; Narishigc, Japan). Fluorescence confocal imaging was performed using an upright Leica DMLFSA microscope with long distance water-dipping lens (Leica HXC APO 20× 0.5 W). Corneal grafts were visualized using reflected laser light (backscatter). For imaging analysis, Z-stacks of 512× 512 pixels (0.1-0.75 μm/pixel) xy sections with 5 μm z-spacing were acquired using the resonant scanner. Z-stack images were denoised and contrast-enhanced using Volocity software (PerkinElmer). The z-stack thickness was adjusted to span the whole thickness of the imaged cornea.

Figure 8:
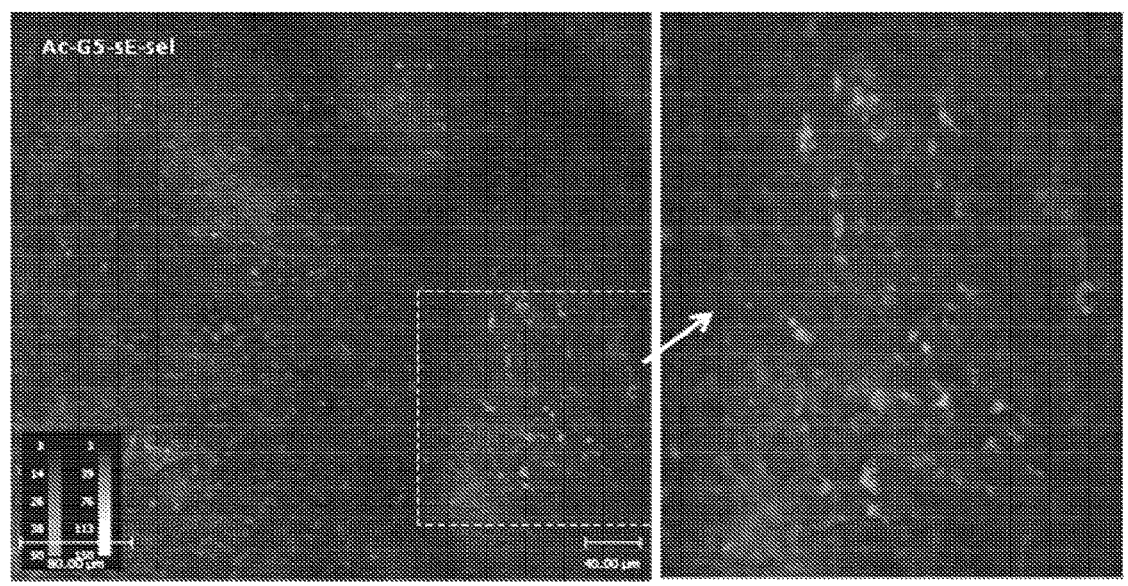
FIG. 8. Recruitment of Ac-G5-sE-sel coated BMC into grafted corneas. C57BL/6 donors received syngeneic corneal transplants. On day 14 post transplantation, mice received 1 million EGFP$^+$ BMC coated either with Ac-G5-BSA or Ac-G5-sE-sel via tail vein injections and the confocal images of the live mice were taken in the next morning. (A) shows the recruitment of Ac-G5-sE-sel coated EGFP$^+$ BMC versus that of Ac-G5-BSA coated control cells (B). (C) shows the relative intensity of EGFP$^+$+cells recruited in the corneas upon BMC infusion.
Figure 8:
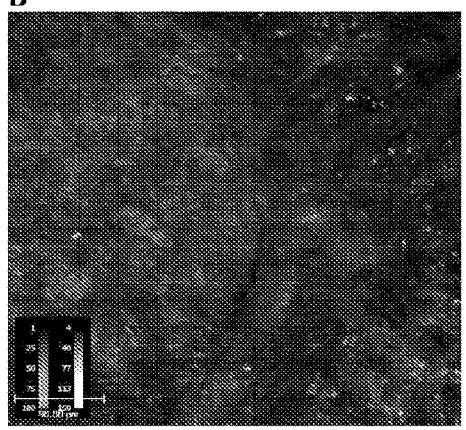
Figure 8:
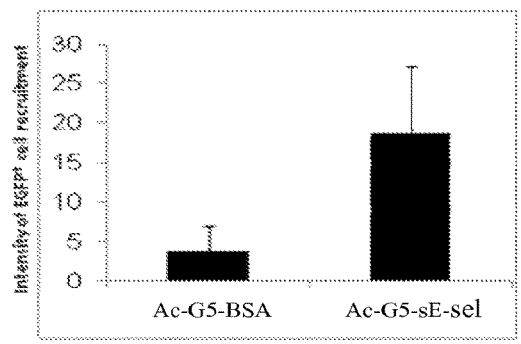

In vivo confocal images took on the next morning showed clearly a sharp increase in EGFP cells homed into the surgically injured corneas of mice that received cells decorated with the Ac-G5-sE-sel (p<0.04, FIG. 8) compared with Ac-G5-BSA. Of note, the undisrupted contralateral corneas did not show cell uptake (data not shown). Thus, these results demonstrated in a second model, the effectiveness of our specified nanocarries in mediating targeted cell delivery in vivo with systemic cell administration.

Figure 9:
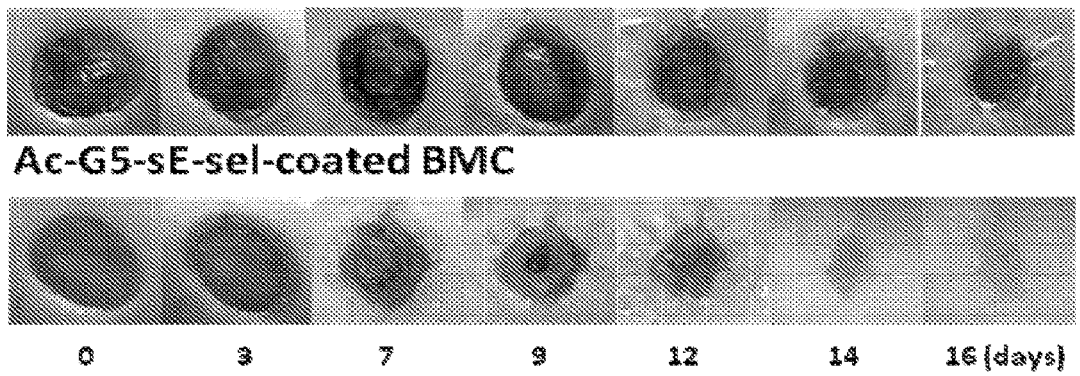
FIG. 9. Promotion of wound healing by local injection of bone marrow cells (BMC) coated with AcG5-sE-sel. BMC derived from diabetic mice (db/db) were coated with Ac-G5-sE-sel or Ac-G5-BSA. When injected in the wound bed, BMC coated with Ac-G5-sE-sel significantly expedited the wound healing process. (A) Representative images of wounds. (B) Wound healing rate. Data are percentage of mean±SD from each group (n=8 mice/group). (C) Representative images of H&E staining of wound tissue sections.
Figure 9:
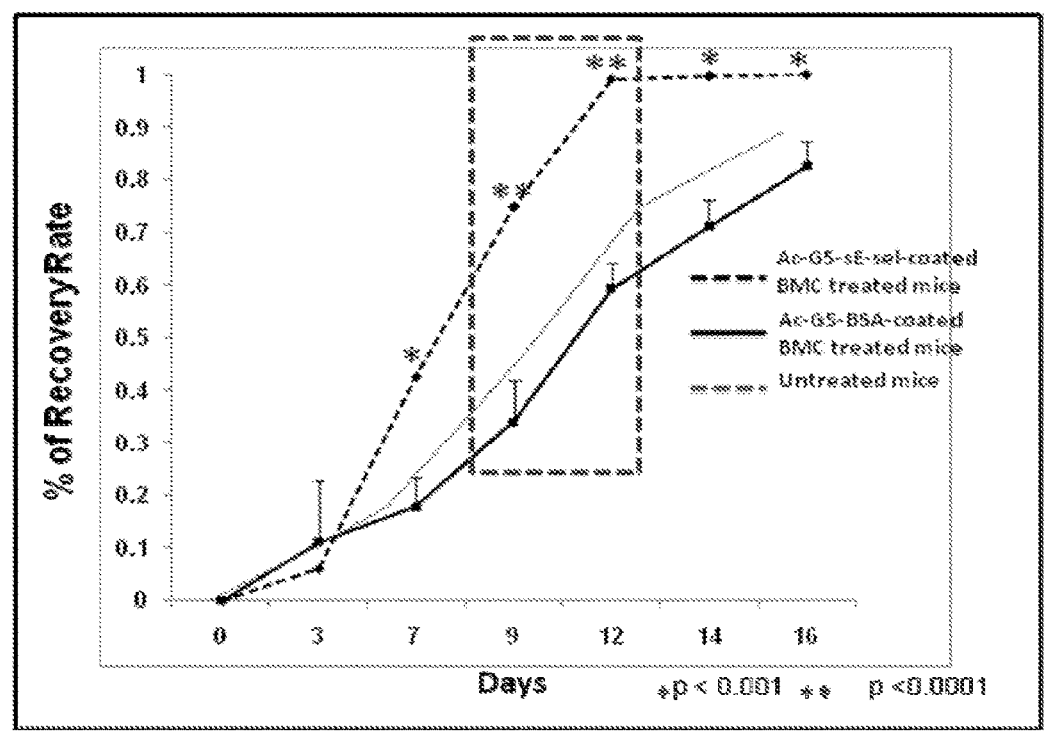
Figure 9:
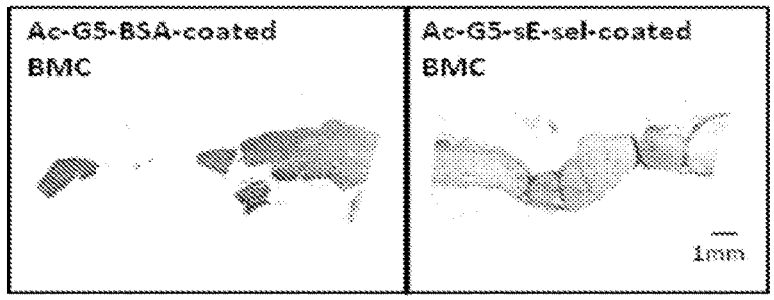
Figure 10:
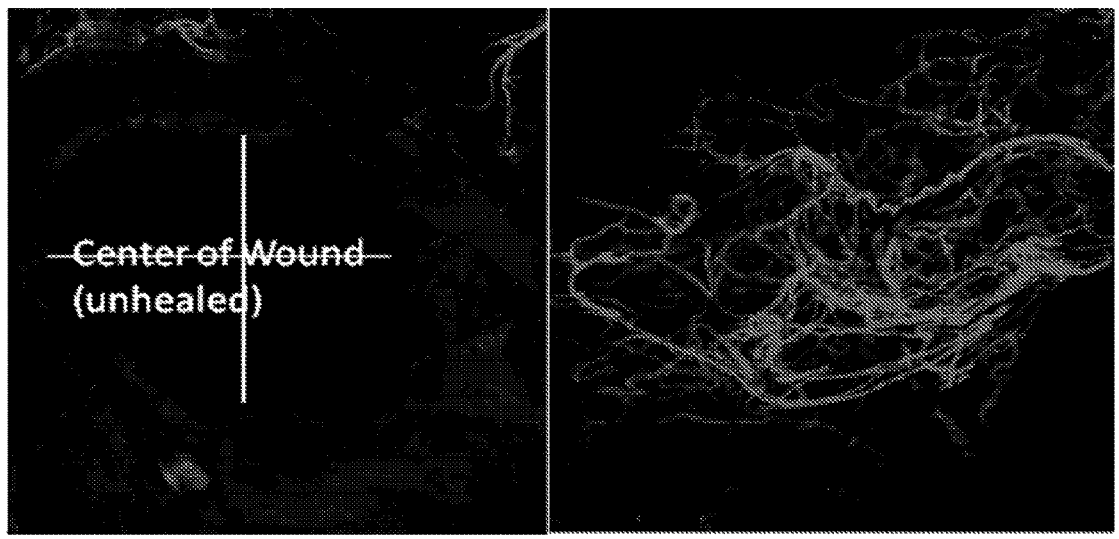
FIG. 10. Promotion of wound neovascularization by local injection of bone marrow cells (BMC) coated with AcG5-sE-sel. BMC derived from diabetic mice (db/db) were coated with Ac-G5-sE-sel or Ac-G5-BSA. When injected in the wound bed, BMC coated with Ac-G5-sE-sel significantly expedited wound neovascularization. (A) Representative confocal microscopy images of blood vessels stained by whole perfusion with Dil dye (B) Vessel density calculated based in red signals. Data are percentage of mean±SD from each group (n=8 mice/group).
Figure 10:
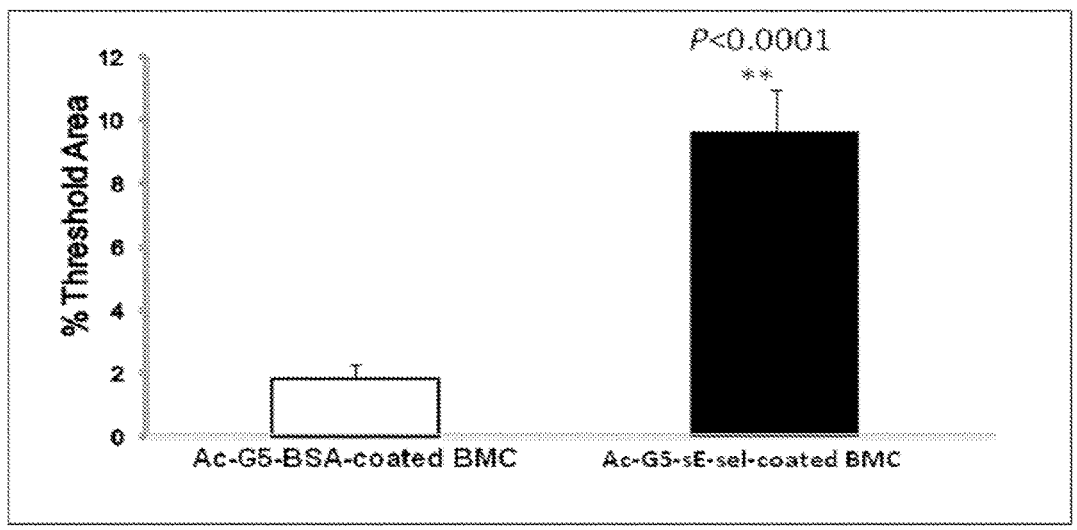
Figure 11:
FIG. 11. Wound bed injection of (A) Ac-G5-sE-sel-coated BMC significantly increases vessel density and promotes engraftment of bone marrow-derived EPC-like cells into diabetic wounds compared to (B) Ac-G5-BSA-coated BMC. Presence of EPC-like cells within diabetic sound vessels are determined by co-expression (yellow) of Dil dye (red) and CD34 (green) as detected by imunostaining.
Figure 11:
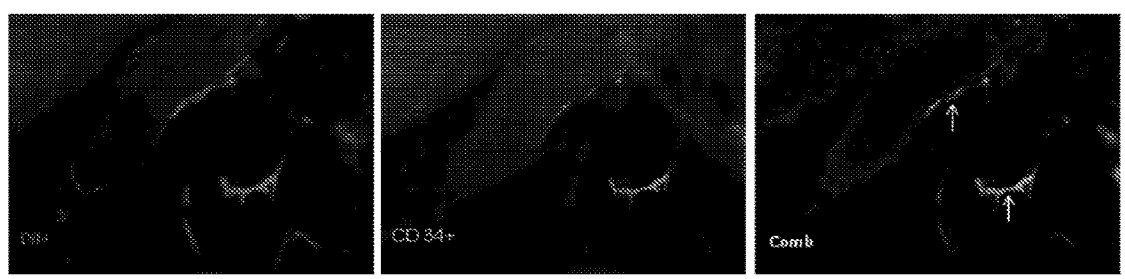

Example 6: Wound Bed Injection of Ac-G5-sE-sel Conjugate Coated BMC in Diabetic Mice To further explore the versatility of this concept of using cells decorated with the Ac-G5-sE-sel dendrimer conjugates for specific cell delivery to tissues undergoing repair, a diabetic mouse model was used. In these experiments, BMC derived from diabetic mice (db/db) were coated with Ac-G5-sE-sel, as described in Example 5. Wound beds of the mice were performed as described in Castilla et al., *Ann. Surg.* 256:560-72 (2012). Ac-G5-sE-sel/BMC or Ac-G5-BSA/BMC were injected into the wound beds, as described in Castilla et al. Wound beds injected with Ac-G5-sE-sel/BMC healed significantly quicker (FIG. 9), had significantly expedited neovascularizaion (FIG. 10), and significantly increased vessel density and engraftment of bone marrow-derived EPC-like cells into diabetic wounds (FIG. 11), as compared to wound beds injected with Ac-G5-BSA/BMC.

Figure 12:
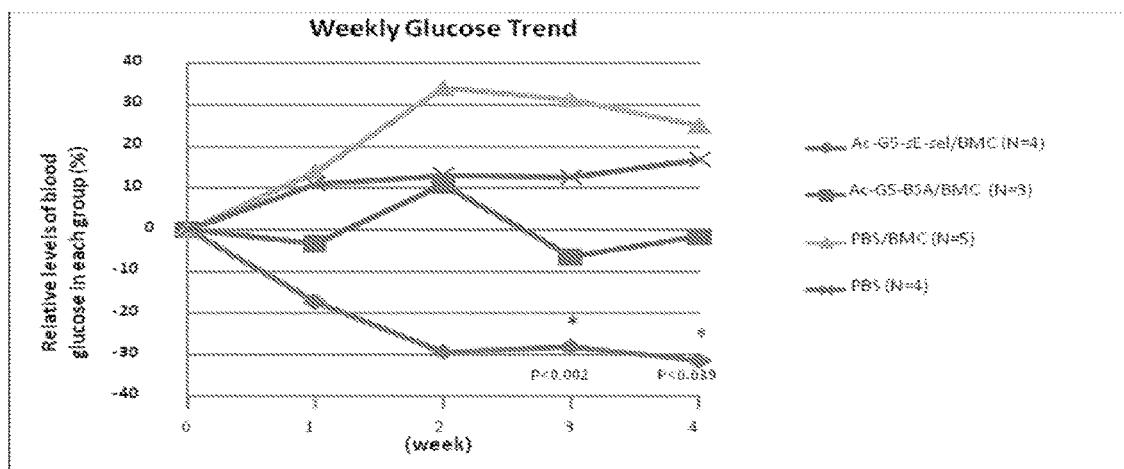
FIG. 12. Therapeutic effect of Ac-G5-sE-sel-coated BMC on diabetes.

The therapeutic effect of Ac-G5-sE-sel-coated BMC on diabetic mice as determined by glucose levels is depicted in FIG. 12. The diabetic mice were divided into four groups, in which group 1 was administered Ac-G5-sE-sel/BMC, while the 3 remaining groups were controls (administered Ac-G5-BSA/BMC, PBC/BMC, or PBS). Glucose levels in the mice were determined by a glucometer. The normalized change of glucose level in each group (%) was calculated as follows: weekly glucose change (blood glucose level (GL) at week when it was measured (week x)-GL a week 0 (week 0, initial GL) divided by normalized glucose change at week 0 (GL at week 0-100 mg/dL). 100 mg/dL is the background level of GL (normal glucose level). It is subtracted from GL at week 0 to determine the initial glucose level after STZ injection is given 4 days ago.

For the following weeks, blood glucose changes are compared changes are compared with the initial level of GL to determine a normalized % using the formula (GL at week x-G1 at week 0)/(GL at week 0-100) This normalization adjusts for the confounding factor that each individual mouse has a different starting point in glucose level (e.g. Group 1 GL at week 0=300 mg/dL, Group 2 GL at week 0=500 mg/dL). Threshold for GL to be defined as diabetes was set as >250 mg/dL. Initial GL after STZ induction ranged from 327-599 mg/dL among different groups. The results show the therapeutic effect of Ac-G5-sE-sel/BMC in reducing the level of blood glucose in the subjects.

The examples demonstrate an innovative cell delivery system for coating cells to be delivered with dendrimers that direct cell homing to targeted tissues. Once transported to the capillaries in the targeted tissues via the circulation, the coated cells can attach to the luminal EC lining of the capillaries through association with the corresponding counterpart of adhesion molecule, which are highly or selectively expressed on the endothelium in the injured or dysfunctional tissues due to local increased cytokines/chemokines resulting from injury, inflammation or tumor.

The experiments demonstrated the feasibility, efficacy and non-toxicity of this new method using human cells, in vitro, and murine cutaneous wound, cornea transplantation and diabetic models. This platform (dendrimer-payloads) and the overall concept of decorating cells with Ac-G5-Adhesion Protein or Peptide, can be applied to many clinically-relevant cell-based treatments for unsolved human diseases such as delayed diabetic wound healing, coronary artery disease, peripheral vascular disease, congestive heart failure, any transplantation or regenerative medicine cell-based approach, and even potentially, to control growth in some tumors).

The experiments show a dendrimer-conjugate, i.e. Ac-G5-sE-sel dendrimer, that mediates cell-cell interactions, bone marrow-derived cell homing, tissue-targeted cell delivery, angiogenesis, cutaneous wound healing, and corneal tissue repair with no evidence of toxicity in murine models, in vivo, or human cells, in vitro. Moreover, the induction of faster than normal healing in C57BL6 mice (that are theologically endowed with particularly robust healing cascades, at a baseline) is the first demonstration that faster healing rates can be mediated by augmenting naturally occurring mechanisms such as bone marrow-derived regenerative cell participation in cutaneous wound healing. The developed and tested specific dendrimers and general concepts have wide spread applicability and high impact.

Thus, presented herein is a dendrimer-mediated cell delivery method by coating a cell surface with dendrimers conjugated to adhesion molecules, e.g. adhesion molecules conjugated to acetylated (Ac) Generation 5 (G5) polyamidoamine (PAMAM) dendrimers. Dendrimers generated under optimized condition are able to sustain their attachment on cell surface for at least around three hours, sufficient to mediate cell homing to a specific desired tissue location. This membrane-bounded dendrimer conjugate functions as an anchor to home decorated cells to luminal endothelial cells (EC) through association with the corresponding receptor(s)/ligand(s) highly or selectively expressed on the endothelium in dysfunctional or inflamed tissues or tissues undergoing a healing cascade. The feasibility and efficacy of delivery of bone marrow cells (BMC) to cutaneous wound tissues and grafted corneas, respectively, for wound healing and neovascularization in mouse models is demonstrated and represents a versatile platform for targeted delivery of therapeutic and/or regenerative cells.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the present invention described herein. Such equivalents are intended to be encompassed by the following claims.

The invention claimed is:

1. A method for promoting ocular tissue repair in a subject in need thereof comprising administering to the subject a composition comprising a cell coated with a conjugate, wherein the conjugate comprises a poly(amidoamine) (PAMAM) dendrimer conjugated to a cell adhesion molecule (CAM), wherein the CAM is an immunoglobulin superfamily CAM (IgSF CAM), addressin, integrin, cadherin or selectin, and wherein the PAMAM dendrimer is an acetylated generation 5 (G5) PAMAM dendrimer.

2. The method of claim 1, wherein the cell is a bone-marrow-derived mononuclear cell (BMC).

3. The method of claim 1, wherein the CAM is selectin.

4. The method of claim 1, wherein the composition further comprises a pharmaceutically acceptable carrier.

5. The method of claim 1, wherein the composition is administered intraocularly, intravenously, subcutaneously, intraperitoneally or topically.

6. The method of claim 5, wherein the intraocular administration comprises intravitreal, subconjunctival or subtenon injection.

7. The method of claim 1, wherein the composition is administered by grafting or transplantation.

8. The method of claim 1, wherein the composition is a gel, matrix or liquid.

9. The method of claim 1, wherein the ocular tissue repair comprises neovascularization.

10. The method of claim 1, wherein the ocular tissue is corneal tissue.

\* \* \* \* \*